United States Patent
Butler et al.

(10) Patent No.: US 10,426,632 B2
(45) Date of Patent: Oct. 1, 2019

(54) EXPANDABLE SPINAL INTERBODY ASSEMBLY

(71) Applicant: Life Spine, Inc., Huntley, IL (US)

(72) Inventors: Michael S. Butler, St. Charles, IL (US); Madeline Wolters, Carol Stream, IL (US); Daniel Predick, Chicago, IL (US); Eugene Shoshtaev, Del Mar, CA (US)

(73) Assignee: Life Spine, Inc., Huntley, IL (US)

( * ) Notice: Subject to any disclaimer, the term of this patent is extended or adjusted under 35 U.S.C. 154(b) by 82 days.

(21) Appl. No.: 15/497,044

(22) Filed: Apr. 25, 2017

(65) Prior Publication Data
US 2017/0224504 A1 Aug. 10, 2017

Related U.S. Application Data

(63) Continuation-in-part of application No. 14/714,821, filed on May 18, 2015, now Pat. No. 9,801,733,
(Continued)

(51) Int. Cl.
A61F 2/44 (2006.01)
A61B 17/88 (2006.01)
A61F 2/30 (2006.01)

(52) U.S. Cl.
CPC .............. *A61F 2/447* (2013.01); *A61F 2/446* (2013.01); *A61F 2002/3037* (2013.01);
(Continued)

(58) Field of Classification Search
CPC ........................................................ A61F 2/44
See application file for complete search history.

(56) References Cited

U.S. PATENT DOCUMENTS 4,466,426 A 8/1984 Blackman
4,636,217 A 1/1987 Ogilvie et al.
(Continued)

FOREIGN PATENT DOCUMENTS

WO WO 2006/102485 9/2006
WO WO 2006/105437 A2 10/2006
(Continued)

OTHER PUBLICATIONS

Bacfuse® Spinous Process Fusion Plate Surgical Technique, 2011, Pioneer Surgical, 12 pages.
(Continued)

*Primary Examiner* — David W Bates
(74) *Attorney, Agent, or Firm* — Foley & Lardner LLP

(57) ABSTRACT

An expandable implant includes a top support configured to engage a first portion of vertebral bone, a bottom support configured to engage a second portion of vertebral bone, and a control assembly coupled to the top support and the bottom support and configured to control relative movement between the top support and the bottom support. The control assembly includes a control member including a head and a body portion. The head includes a recess and the body portion includes at least one access port in fluid communication with the recess to enable delivery of fluid to an interior of the implant via the recess and at least one access port.

18 Claims, 40 Drawing Sheets

Related U.S. Application Data which is a continuation-in-part of application No. 13/802,110, filed on Mar. 13, 2013, now Pat. No. 9,034,041.

(52) U.S. Cl.
CPC ............... *A61F 2002/30387* (2013.01); *A61F 2002/30405* (2013.01); *A61F 2002/30428* (2013.01); *A61F 2002/30433* (2013.01); *A61F 2002/30471* (2013.01); *A61F 2002/30507* (2013.01); *A61F 2002/30515* (2013.01); *A61F 2002/30538* (2013.01); *A61F 2002/30556* (2013.01); *A61F 2002/30579* (2013.01); *A61F 2002/30784* (2013.01); *A61F 2002/30841* (2013.01); *A61F 2002/30904* (2013.01); *A61F 2310/00017* (2013.01); *A61F 2310/00023* (2013.01)

(56) References Cited

U.S. PATENT DOCUMENTS

| | | | |
|---|---|---|---|
| 4,863,476 A | 9/1989 | Shepperd |
| 5,390,683 A | 2/1995 | Pisharodi |
| 5,645,599 A | 7/1997 | Samani |
| 5,658,335 A | 8/1997 | Allen |
| 5,658,337 A | 8/1997 | Kohrs et al. |
| 5,836,948 A | 11/1998 | Zucherman et al. |
| 5,860,977 A | 1/1999 | Zucherman et al. |
| 5,876,404 A | 3/1999 | Zucherman et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,126,689 A | 10/2000 | Brett |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,375,682 B1 | 4/2002 | Fleischmann et al. |
| 6,409,766 B1 | 6/2002 | Brett |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,648,917 B2 | 11/2003 | Gerbec et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,773,460 B2 | 8/2004 | Jackson |
| 6,796,983 B1 | 9/2004 | Zucherman et al. |
| 7,048,736 B2 | 5/2006 | Robinson et al. |
| 7,087,055 B2 | 8/2006 | Lim et al. |
| 7,101,375 B2 | 9/2006 | Zucherman et al. |
| 7,217,291 B2 | 5/2007 | Zucherman et al. |
| 7,621,950 B1 | 11/2009 | Globerman et al. |
| 7,695,513 B2 | 4/2010 | Zucherman et al. |
| 7,731,751 B2 | 6/2010 | Butler et al. |
| 7,879,098 B1 | 2/2011 | Simmons, Jr. |
| 8,016,861 B2 | 9/2011 | Mitchell et al. |
| 8,048,117 B2 | 11/2011 | Zucherman et al. |
| 8,105,382 B2 | 1/2012 | Olmos et al. |
| 8,231,656 B2 | 7/2012 | Lee et al. |
| 8,241,330 B2 | 8/2012 | Lamborne et al. |
| 8,303,663 B2 | 11/2012 | Jimenez et al. |
| 8,343,190 B1 | 1/2013 | Mueller et al. |
| 8,353,963 B2 | 1/2013 | Glerum |
| 8,382,801 B2 | 2/2013 | Lamborne et al. |
| 8,597,360 B2 | 12/2013 | McLuen et al. |
| 8,894,711 B2 | 11/2014 | Varela |
| 8,894,712 B2 | 11/2014 | Varela |
| 9,034,041 B2 | 5/2015 | Wolters et al. |
| 9,532,883 B2 | 1/2017 | McLuen et al. |
| 2002/0128716 A1 | 9/2002 | Cohen et al. |
| 2003/0040746 A1 | 2/2003 | Mitchell et al. |
| 2003/0236520 A1 | 12/2003 | Lim et al. |
| 2004/0153156 A1 | 8/2004 | Cohen et al. |
| 2004/0167625 A1 | 8/2004 | Beyar et al. |
| 2005/0033437 A1 | 2/2005 | Bao et al. |
| 2005/0070911 A1 | 3/2005 | Carrison et al. |
| 2005/0131536 A1 | 6/2005 | Eisermann et al. |
| 2005/0143827 A1 | 6/2005 | Globerman et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0036258 A1 | 2/2006 | Zucherman et al. |
| 2006/0084988 A1 | 4/2006 | Kim |
| 2006/0089718 A1 | 4/2006 | Zucherman et al. |
| 2006/0095136 A1 | 5/2006 | McLuen |
| 2006/0189999 A1 | 8/2006 | Zwirkoski |
| 2006/0241601 A1 | 10/2006 | Trautwein et al. |
| 2006/0264938 A1 | 11/2006 | Zucherman et al. |
| 2007/0142915 A1 | 6/2007 | Altarac et al. |
| 2008/0114456 A1 | 5/2008 | Dewey et al. |
| 2008/0140207 A1 | 6/2008 | Olmos et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0312741 A1 | 12/2008 | Lee et al. |
| 2009/0062915 A1 | 3/2009 | Kohm et al. |
| 2010/0179655 A1* | 7/2010 | Hansell et al. ........... A61F 2/44 623/17.11 |
| 2010/0211176 A1 | 8/2010 | Greenhalgh |
| 2010/0241167 A1 | 9/2010 | Taber et al. |
| 2011/0022090 A1 | 1/2011 | Gordon et al. |
| 2011/0066186 A1 | 3/2011 | Boyer et al. |
| 2011/0144692 A1 | 6/2011 | Saladin et al. |
| 2011/0172709 A1 | 7/2011 | Lyons et al. |
| 2011/0184468 A1 | 7/2011 | Metcalf et al. |
| 2011/0224731 A1 | 9/2011 | Smisson et al. |
| 2011/0282453 A1 | 11/2011 | Greenhalgh et al. |
| 2011/0319997 A1 | 12/2011 | Glerum et al. |
| 2012/0016418 A1 | 1/2012 | Chin et al. |
| 2012/0059474 A1 | 3/2012 | Weiman |
| 2012/0109203 A1 | 5/2012 | Dryer et al. |
| 2012/0221051 A1 | 8/2012 | Robinson |
| 2012/0330422 A1 | 12/2012 | Weiman |
| 2013/0085572 A1 | 4/2013 | Glerum et al. |
| 2013/0103156 A1 | 4/2013 | Packer et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0211526 A1 | 8/2013 | Alheidt et al. |
| 2014/0148904 A1 | 5/2014 | Robinson |
| 2014/0236296 A1 | 8/2014 | Wagner et al. |
| 2014/0277473 A1 | 9/2014 | Perrow |
| 2014/0277500 A1 | 9/2014 | Logan et al. |
| 2014/0343678 A1 | 11/2014 | Suddaby et al. |
| 2015/0100128 A1 | 4/2015 | Glerum et al. |
| 2015/0173917 A1 | 6/2015 | Radcliffe et al. |
| 2016/0242927 A1 | 8/2016 | Seifert et al. |
| 2017/0056197 A1 | 3/2017 | Weiman et al. |
| 2017/0333198 A1 | 11/2017 | Robinson |
| 2018/0318101 A1 | 11/2018 | Engstrom |

FOREIGN PATENT DOCUMENTS

| | | |
|---|---|---|
| WO | WO 2009/124269 | 10/2009 |
| WO | WO 2016/077610 | 5/2016 |
| WO | WO 2016/127139 A1 | 8/2016 |
| WO | WO 2017/027873 A1 | 2/2017 |
| WO | WO 2017/066463 A1 | 4/2017 |

OTHER PUBLICATIONS

Extended European Search Report for European Application No. 14159101.6, dated Jun. 18, 2014, 6 pages.
Extended European Search Report for European Application No. 16169890.7, dated Oct. 21, 2016, 7 pages.
International Preliminary Report on Patentability for Application No. PCT/US06/12060, date of completion Jul. 18, 2007, 3 pages.

(56) References Cited

OTHER PUBLICATIONS

International Search Report and Written Opinion for International Application No. PCT/US2012/057324, dated Dec. 20, 2012, 10 pages.
International Search Report for Application No. PCT/US06/12060, dated Apr. 5, 2007, 1 page.
Written Opinion of the International Searching Authority for Application No. PCT/US06/12060, dated Apr. 5, 2007, 3 pages.
Search Report for International Application No. PCT/US2018/029120, dated Jun. 28, 2018, 17 pages.
Search Report for International Application No. PCT/US2018/029149, dated Jun. 25, 2018, 13 pages.
Search Report for International Application No. PCT/US2018/041306, dated Sep. 28, 2018, 12 pages.

* cited by examiner (A-A)

EXPANDABLE SPINAL INTERBODY ASSEMBLY

CROSS-REFERENCE TO RELATED PATENT APPLICATIONS

This application is a continuation-in-part of U.S. application Ser. No. 14/714,821, filed May 18, 2015, which is a continuation-in-part of U.S. application Ser. No. 13/802,110, filed Mar. 13, 2013, both of which are incorporated herein by reference in their entireties. This application is related to U.S. application Ser. No. 15/497,011, filed Apr. 25, 2017, entitled "Expandable Spinal Interbody Assembly," filed on the same day as the present application, and which is incorporated herein by reference in its entirety.

BACKGROUND

The present disclosure relates to spinal interbody and intravertebral body devices and, more particularly, to vertebral interbody and intravertebral devices that are expandable after spinal placement thereof.

Fusion cages, as well as other types of bodies and/or devices, are frequently utilized in spinal surgery inside a vertebra (intravertebral) and/or between vertebrae of a patient (interbody). With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posteriolaterally.

A problem with most spinal interbody and intravertebral devices is that they are static in size. This poses various problems with their use and/or implantation. Particularly, static sized spinal devices are fairly large in order to properly bridge the gap between adjacent vertebrae. This large size does not lend itself to microsurgery, arthroscopic surgery or the like.

A few interbody devices, however, are now being made that are expandable. Expandable interbody devices allow the interbody device to be initially smaller than traditional non-expandable (static) interbody devices such that expandable interbody devices may be more easily inserted or implanted into the vertebral space. Moreover, expandable interbody devices allow the surgeon to set the amount of expansion necessary for the particular patient rather than the static interbody device dictating the spacing.

SUMMARY

One embodiment relates to an expandable implant, comprising a top support assembly defining an upper surface configured to engage a first portion of vertebral bone; a bottom support assembly defining a lower surface configured to engage a second portion of vertebral bone; a control assembly coupled to the top support assembly and the bottom support assembly and configured to control relative movement between the top support assembly and the bottom support assembly between a collapsed position and an expanded position; wherein in the collapsed position, the upper surface is generally parallel to the lower surface, and wherein in the expanded position, a portion of the upper surface extends at an acute angle relative to a portion of the lower surface.

Another embodiment relates to an expandable implant comprising a top support assembly defining an upper surface configured to engage a first portion of vertebral bone; a bottom support assembly defining a lower surface configured to engage a second portion of vertebral bone; a first wedge member slidably coupled to the top and bottom support assemblies; a second wedge member slidably coupled to the top and bottom support assemblies; and a control assembly coupled to the first and second wedge members and configured to control relative movement between the top support assembly and the bottom support assembly between a collapsed position and an expanded position; wherein in the collapsed position, the upper surface is generally parallel to the lower surface, and wherein in the expanded position, a portion of the upper surface extends at an angle relative to a portion of the lower surface.

Another embodiment relates to a method of using an expandable implant, comprising providing an expandable implant comprising a top support assembly, a bottom support assembly, and a control assembly coupled to the top and bottom support assemblies; manipulating the control assembly in a first manner to move the top support assembly in a linear fashion relative to the bottom support assembly; and manipulating the control assembly in a second manner to move at least a portion of the top support assembly in a non-linear fashion relative to at least a portion of the bottom support assembly.

Another embodiment relates to an expandable implant, comprising a top support configured to engage a first portion of vertebral bone; a bottom support configured to engage a second portion of vertebral bone; and a control assembly coupled to the top support and the bottom support and configured to control relative movement between the top support and the bottom support, wherein the control assembly includes a control member including a head and a body portion; and wherein the head includes a recess and the body portion includes at least one access port in fluid communication with the recess to enable delivery of fluid to an interior of the implant via the recess and at least one access port.

Another embodiment relates to an expandable implant, comprising a top support including a top surface configured to engage a first portion of vertebral bone; a bottom support including a bottom surface configured to engage a second portion of vertebral bone, wherein the top and bottom surfaces define a taper; and a control assembly coupled to the top support and the bottom support and configured to control relative movement between the top support and the bottom support, wherein the control assembly includes a control member having a recess and at least one access port in fluid communication with the recess to enable delivery of fluid to an interior of the implant via the recess and at least one access port.

Another embodiment relates to an implant comprising a top support configured to engage a first portion of vertebral bone; a bottom support configured to engage a second portion of vertebral bone; and a control assembly coupled to the top support and the bottom support and configured to control relative movement between the top support and the bottom support, wherein the control assembly includes a front portion configured to slidably engage the top and bottom supports; a rear portion configured to slidably engage the top and bottom supports; and a control member including a head disposed within the rear portion, and a threaded portion threadingly engaging the front portion; wherein the head includes a recess and at least one access port in fluid communication with the recess to enable delivery of fluid to an interior of the implant via the recess and at least one access port.

BRIEF DESCRIPTION

The foregoing and other features of the present invention will become more apparent to one skilled in the art upon also reading the following description of embodiments with reference to the accompanying drawings.

Figure 1:
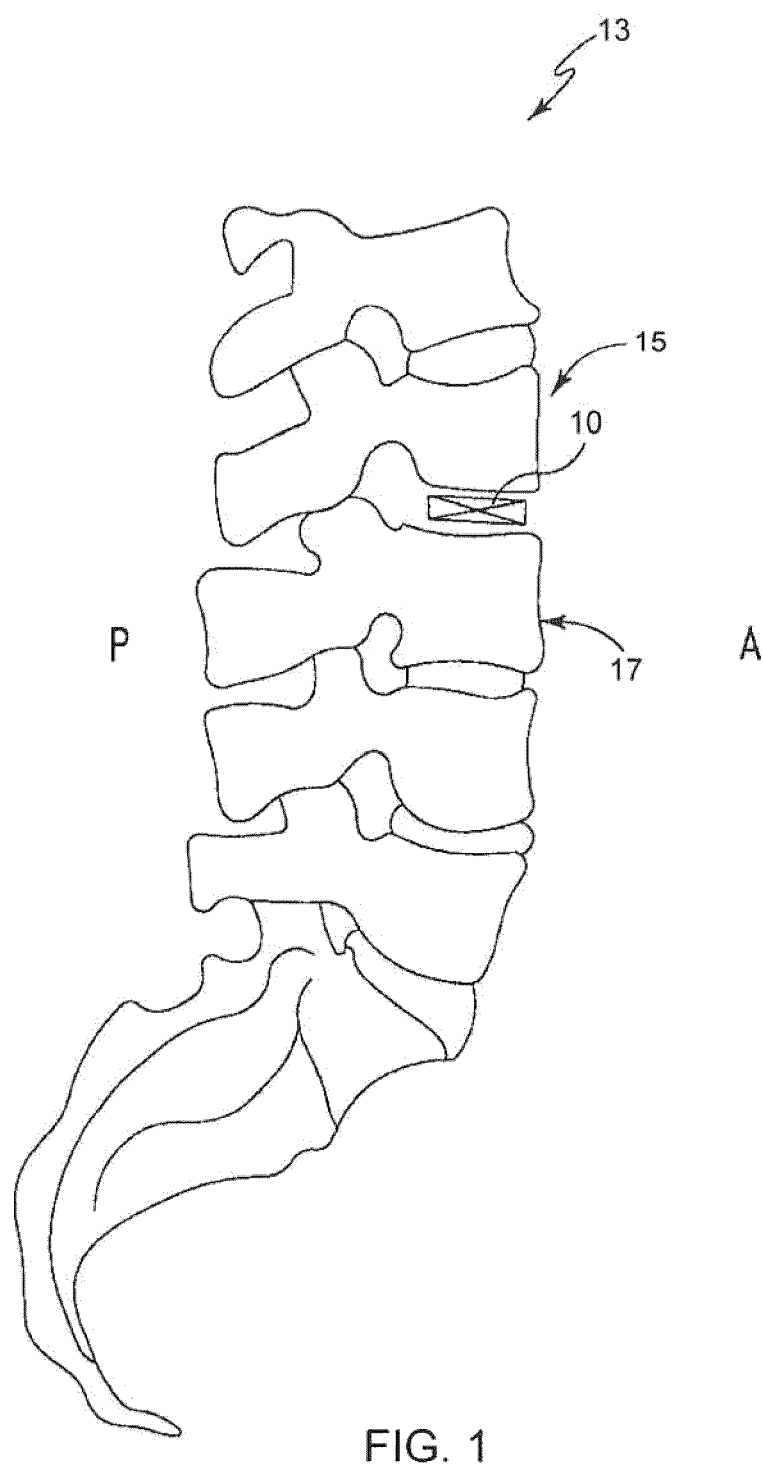
FIG. 1 is a side view of a portion of a human spine illustrating inter-vertebral placement of an expandable inter-body/intravertebral body device in accordance with the principles of the present invention.
Figure 2:
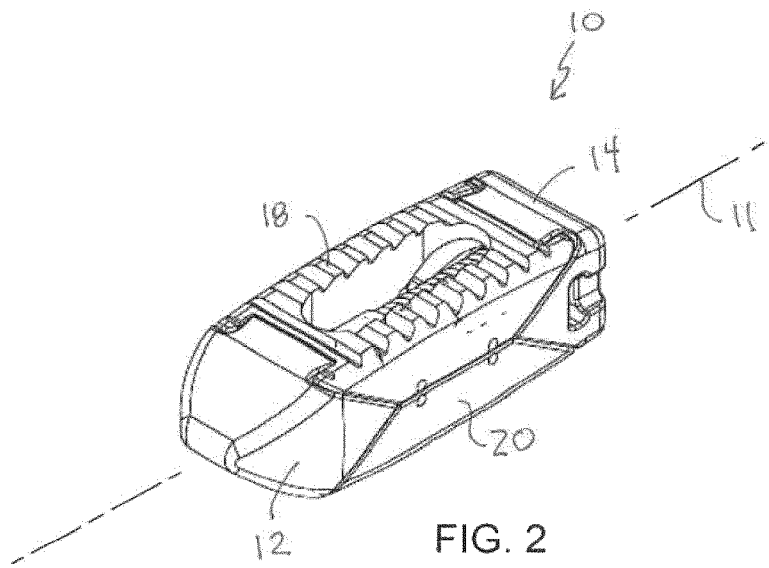
FIGS. 2-15 show various views of an expandable implant according to one embodiment.
Figure 3:
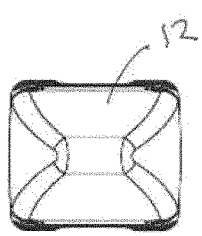
Figure 4:
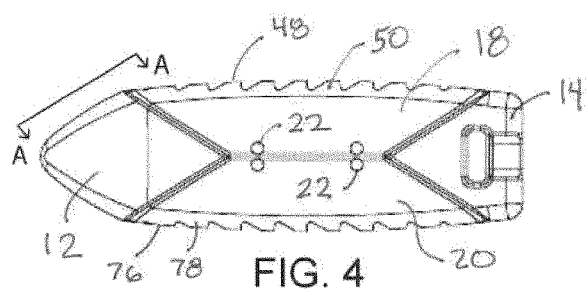
Figure 5:
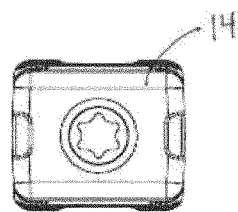
Figure 6:
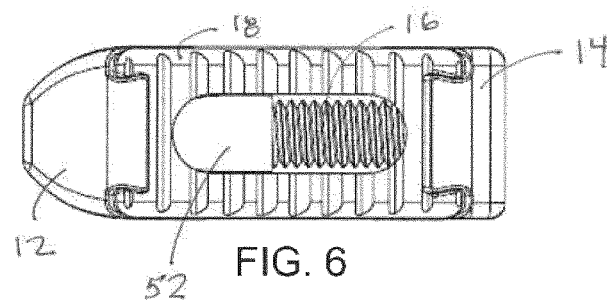
Figure 7:
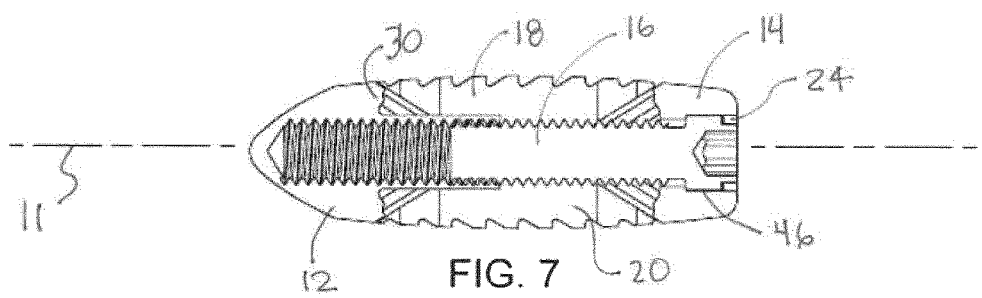
Figure 8:
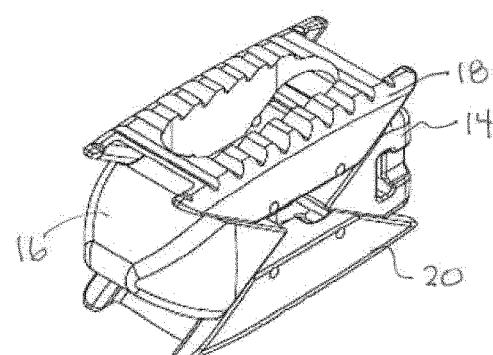
Figure 9:
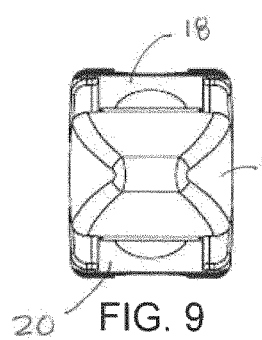
Figure 10:
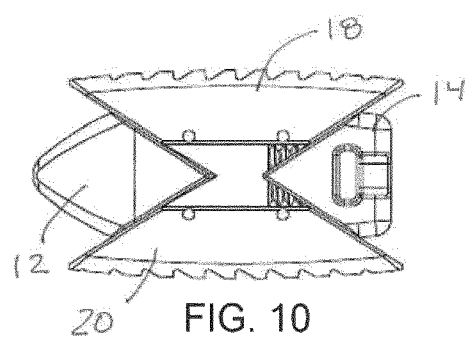
Figure 11:
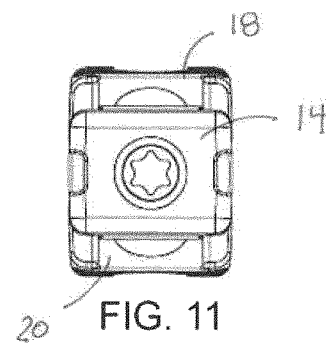
Figure 12:
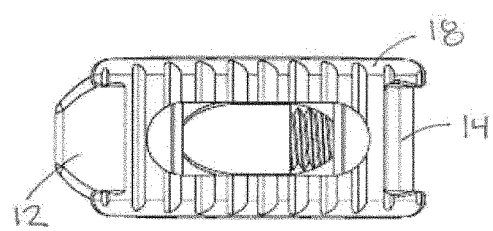
Figure 13:
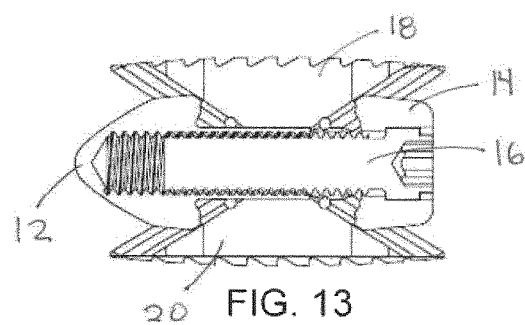

Corresponding reference characters indicate corresponding parts throughout the several views. Although the drawings represent embodiments of the invention, the drawings are not necessarily to scale and certain features may be exaggerated in order to better illustrate and explain the principles of the present invention. The exemplifications set out herein illustrate several embodiments of the invention, but the exemplifications are not to be construed as limiting the scope of the invention in any manner.

DETAILED DESCRIPTION

The present disclosure relates to expandable and/or dynamic interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (collectively hereinafter, spinal device(s)) for providing support, stabilization and/or promoting bone growth between or inside vertebrae that have been destabilized or otherwise due to injury, illness and/or the like. Particularly, the present disclosure provides various versions of dynamic (expandable and/or expandable and retractable) interbody/intravertebral body devices that are usable in a spinal column of a human.

As representative of each one of the various versions of the present invention, FIG. 1 illustrates a representative dynamic spinal body device or expandable implant 10. The implant 10 is depicted as implanted or inserted into a human spine 13 of which only a lower portion of the spine 13 is shown. The implant 10 is illustrated implanted between adjacent upper and lower vertebrae 15, 17 of the spine 13 in FIG. 1 (hence interbody or intervertebral). Vertebrae 15 and 17 have portions that face anteriorly ("A", and from the right as viewed in FIG. 1) and portions that face posteriorly ("P", and from the left as viewed in FIG. 1).

According to various exemplary embodiments, the components of implant 10 may be made of any suitable material(s), including a variety of metals, plastics, composites, or other suitable bio-compatible materials. In some embodiments, one or more components of implant 10 may be made of the same material, while in other embodiments, different materials may be used for different components of implant 10.

Referring now to FIGS. 2-15, expandable implant 10 is shown according to an exemplary embodiment. Implant 10 is usable, for example, between and/or within vertebral bodies of the spine, and may share many of the features of the other inter/intra-body implants discussed elsewhere herein. It should be understood that implant 10 may in some embodiments be usable in other portions of the body in addition to the spine, and all such applications are to be understood to be within the scope of the present disclosure.

According to an exemplary embodiment, implant 10 includes a first, or front portion 12 (e.g., a first wedge member), a second, or rear portion 14 (e.g., a second wedge member), and a third, intermediate, or control member or portion 16, which collectively form a body or control assembly that extends along a longitudinal axis 11 of implant 10. A first, or upper support 18 (e.g., an upper plate, support member, assembly, etc.) and a second, lower support 20 (e.g., a lower plate, support member, assembly), are coupled to the body assembly and extend generally between front and rear portions 12, 14. According to an exemplary embodiment, first and second supports 18, 20 define a height of implant 10 extending between outer or top surface 48 of first support 18 and outer or lower surface 76 of second support 20.

In one embodiment, front portion 12 includes a rounded, or bull nose portion intended to facilitate insertion of implant 10 into a patient. Front portion 12 also includes ramped surfaces 26, 28 and projections 30, 32 that facilitate controlled sliding movement between front portion 12 and first and second supports 18, 20. An aperture 34 may be threaded to receive control member 16 to provide an adjustable control mechanism for implant 10.

Figure 14:
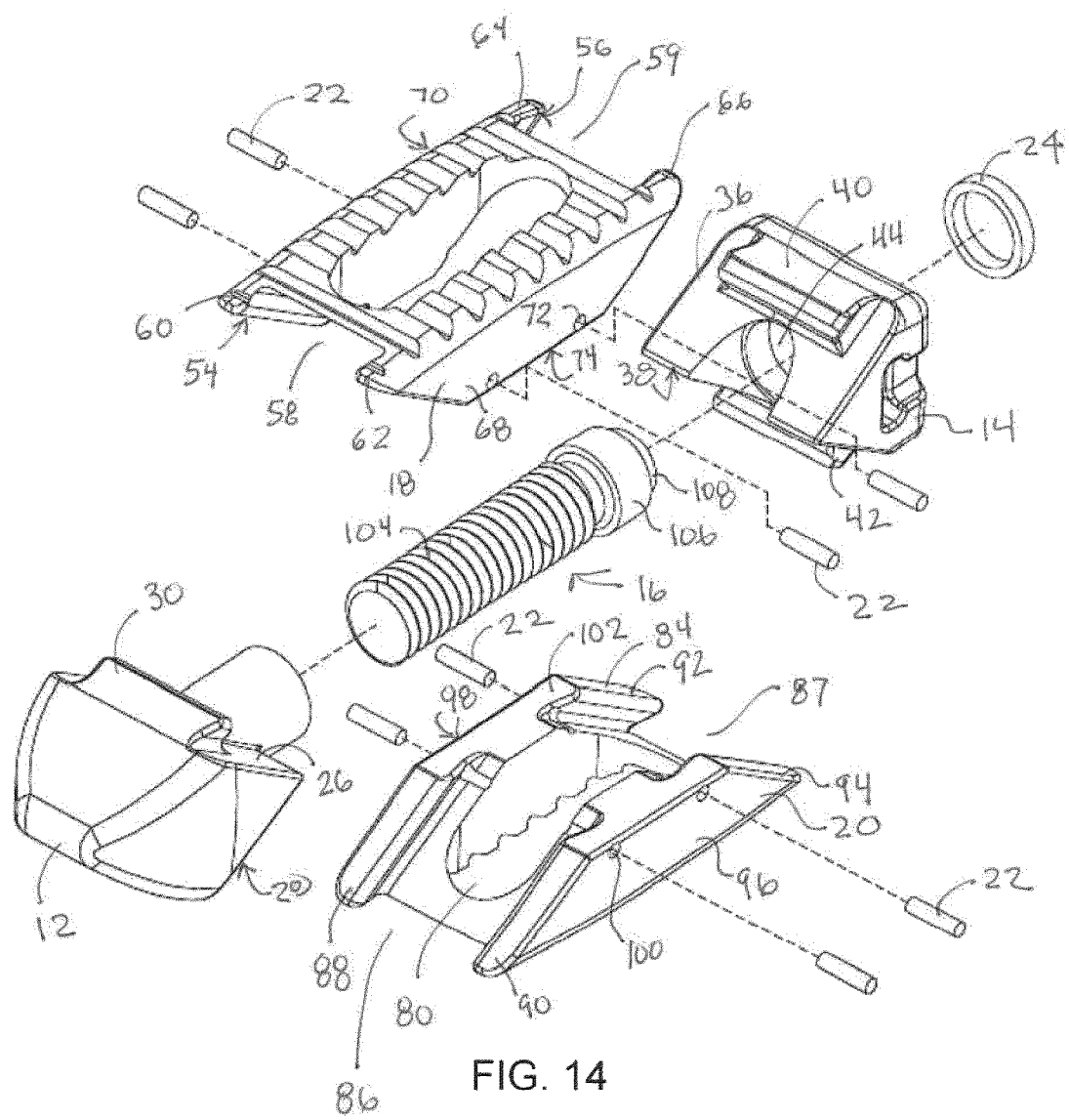
Figure 15:
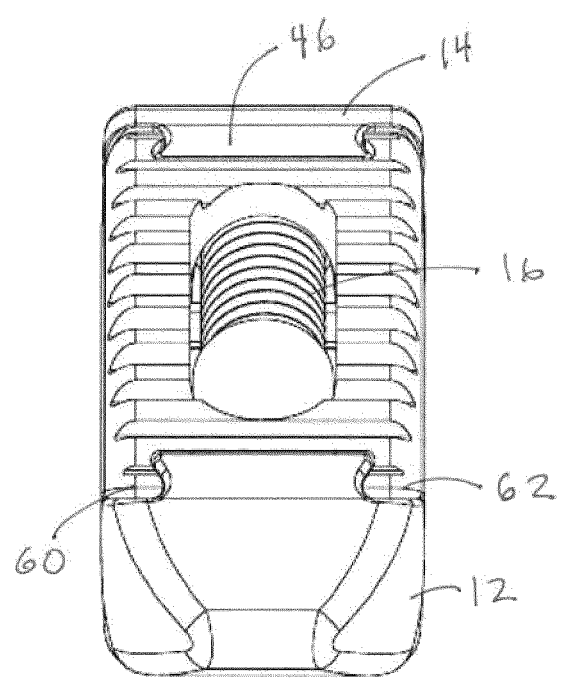

Referring to FIG. 14, ramped surface 26 extends at an angle relative to axis 11, and projection 30 extends upward relative to ramped surface 26. Ramped surface 26 is a generally flat surface configured to engage a correspondingly ramped surface (surface 54) on first support 18. Projection 30 extends laterally across front portion 12. In some embodiments, projection 30 may have a dovetail shape, while in other embodiments, projection 30 may take other shapes, including having an undercut portion, etc. The dovetail shape provides a relatively larger top portion and an undercut lower portion such that front portion 12 and first support 18 can slide relative to one another, but the parts cannot be separated, for example, by merely lifting first support 18 away from front portion 12 (e.g., in an upward direction generally perpendicular to axis 11).

Ramped surface 28 and projection 32 share similar features to ramped surface 26 and projection 30, except that ramped surface 28 and projection 32 interface with corresponding surfaces on second support 20, rather than first support 18. It should be noted that ramped surfaces 26, 28 may be inclined relative to axis 11 to provide any desirable adjustment features, as changing the incline of the ramped surfaces will change the rate at which the first and second support members move up/down.

Referring further to FIG. 14, according to an exemplary embodiment, rear portion 14 includes ramped surfaces 36, 38, projections 40, 42, an aperture, or through-hole 44, and a counterbore 46. Rear portion 14 may define a generally flat rearward-most surface being generally rectangular in shape. In other embodiments, the shape of rear portion 14 may be varied to suit a particular application.

Ramped surface 36 extends at an angle relative to axis 11, and projection 40 extends upward relative to ramped surface 36. Ramped surface 36 is a generally flat surface configured to engage a correspondingly ramped surface (surface 56) on first support 18. Projection 40 extends laterally across rear portion 14. In some embodiments, projection 40 may have a dovetail shape (see, e.g., FIG. 15), while in other embodiments, projection 40 may take other shapes, including having an undercut portion etc. The dovetail shape provides a relatively larger top portion and an undercut lower portion such that rear portion 14 and first support 18 can slide relative to one another, but the parts cannot be separated, for example, by merely lifting first support 18 away from rear portion 14 (e.g., in an upward direction generally perpendicular to axis 11).

Ramped surface 38 and projection 42 share similar features to ramped surface 36 and projection 40, except that ramped surface 38 and projection 42 interface with corresponding surfaces on second support 20, rather than first support 18. It should be noted that ramped surfaces 36, 38 may be inclined relative to axis 11 to provide any desirable adjustment features, as changing the incline of the ramped surfaces will change the rate at which the first and second support members move up/down.

According to an exemplary embodiment, first and second supports 18, 20 are configured to be moveable relative to the body or control assembly (e.g., front and rear portions 12, 14 and control portion 16) such that implant 10 is reconfigurable between a first configuration (e.g., a retracted, collapsed, or minimal configuration), as shown in FIGS. 2-7, and a second configuration (e.g., an expanded or maximum configuration), as shown in FIGS. 8-13 and any intermediate position therebetween. Control member 16 is rotatable and threadingly received by front portion 12 such that rotation of control member 16 in a first (e.g., clockwise) direction causes front and rear portions 12, 14 to move toward each other, thereby causing first and second supports 18, 20 to move outward toward the expanded configuration. Conversely, rotation of control member 16 in a second (e.g., counter-clockwise) direction causes front and rear portions 12, 14 to move away from each other, thereby causing first and second supports 18, 20 to move inward toward the collapsed configuration. It should be noted that in use, control member 16 may be adjusted so as to maintain first and second supports 18, 20 in a fully collapsed configuration, a fully expanded configuration, or any desired configuration or intermediate position therebetween.

First and second supports 18, 20 and front and rear portions 12, 14 have corresponding geometric features (e.g., correspondingly ramped surfaces) such that displacement of front portion 12 relative to rear portion 14 along axis 11 causes relative planar and/or linear displacement of first and second supports 18, 20. As discussed above, the geometric features of the various components may be varied to provide for varying adjustment features for first and second supports 18, 20.

In one embodiment, first and second supports 18, 20 are generally similar in structure. Referring to FIG. 14, first support 18 includes outer, or top surface 48, ramped surfaces 54, 56, channels 58, 59, and two pairs of opposing projections—projections 60, 62, and projections 64, 66. First support 18 further includes sidewalls 68, 70, pin or retaining member apertures 72, and inner, or bottom surface 74. Top surface 48 includes a number of ridges, or projections 50, intended to provide a gripping surface for adjacent vertebrae, and a bone graft cavity, or window 52 intended to provide a space to receive bone graft material.

In use, control member 16 extends through through-hole 44 in rear portion 14 and into front portion 12. Head portion 106 of control member 16 seats in counterbore 46 of rear portion 14, and threaded portion 104 threadingly engages aperture 34 of front portion 12. Head portion 106 may include an annular recess 108 configured such that a collar 24 can be positioned (e.g., press-fit, welded, etc.) into counterbore 46 rearward of head portion 106 to retain control member 16 in place. As a user rotates control member 16, front portion 12 and rear portion 14 move toward/away from each other (depending on the direction of rotation), and first and second supports 18, 20 in turn move away from/toward each other.

As shown in FIG. 14, opposing projections 60, 62 on first support 18 form a recess, or channel 58. In one embodiment, channel 58 has a dovetail shape corresponding in shape to projection 30 on front portion 12. Likewise, projections 64, 66 in first support 18 form channel 59 having a dovetail shape similar in shape to projection 40 on rear portion 14. Projections 30, 40 slide within channels 58, 59 as first support 18 moves up/down. Retaining members or pins 22 extend through first and second supports 18, 20 and act to limit the range of movement of first and second supports 18, 20 relative to front and rear portions 12, 14, and prevent first and second supports 18, 20 from being completely removed from front and rear portions 12, 14.

Second support 20 is similar to first support 18 and includes outer, or bottom surface 76, ramped surfaces 82, 84, channels 86, 87, and two pairs of opposing projections—projections 88, 90, and projections 92, 94. Second support 20 further includes sidewalls 96, 98, pin or retaining member apertures 80, and inner, or top surface 102. Bottom surface 76 includes a number of ridges, or projections 78, intended to provide a gripping surface for adjacent vertebrae, and a bone graft cavity, or window 80 intended to provide a space to receive bone graft material. In one embodiment, the components of second support 20 are similar in structure and function to the corresponding components of first support 18. In other embodiments, the components of second support 20 may provide additional and/or different structural and/or functional features relative to the corresponding components of first support 18.

It should be noted that implant 10 may share various features with the other implants described herein, and be made of the same, similar, or different materials. For example, various components of implant 10 may be made of metal, plastic, composites, or other suitable bio-compatible materials. Further, implant 10 may be usable in connection with the spine or other parts of the body.

Referring now to FIGS. 16-30, an expandable implant 110 is shown according to an exemplary embodiment. Implant 110 is usable, for example, between and/or within vertebral bodies of the spine, and may share many of the features of the other inter/intra-body implants discussed elsewhere herein. It should be understood that implant 110 may in some embodiments be usable in other portions of the body in addition to the spine, and all such applications are to be understood to be within the scope of the present disclosure.

Implant 110 is generally similar to implant 10 in structure and function except with respect to the additional alignment features discussed below.

According to an exemplary embodiment, implant 110 includes a first, or front portion 112, a second, or rear portion 114, and a third, intermediate, or control member or portion 116, which collectively form a body or control assembly that extends along a longitudinal axis 111 of implant 110. A first, or upper support 118 (e.g., an upper plate or support member, etc.) and a second, lower support 120 (e.g., a lower plate or support member), are coupled to the body or control assembly and may extend generally between front and rear portions 112, 114. According to an exemplary embodiment, first and second supports 118, 120 define a height of implant 110 extending between outer or top surface 148 of first support 118 and outer or lower surface 176 of second support 120.

In one embodiment, front portion 112 includes a rounded, or bull nose portion intended to facilitate insertion of implant 110 into a patient. Front portion 112 also includes ramped surfaces and projections (e.g., similar to ramped surfaces 26, 28 and projections 30, 32) that facilitate controlled sliding movement between front portion 112 and first and second supports 118, 120. An aperture may be threaded to receive control member 116 to provide an adjustable control mechanism for implant 110.

Figure 20:
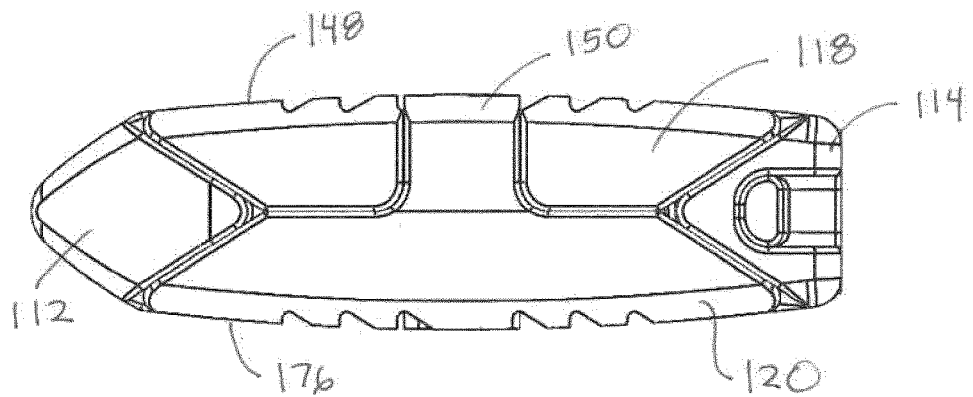
Figure 21:
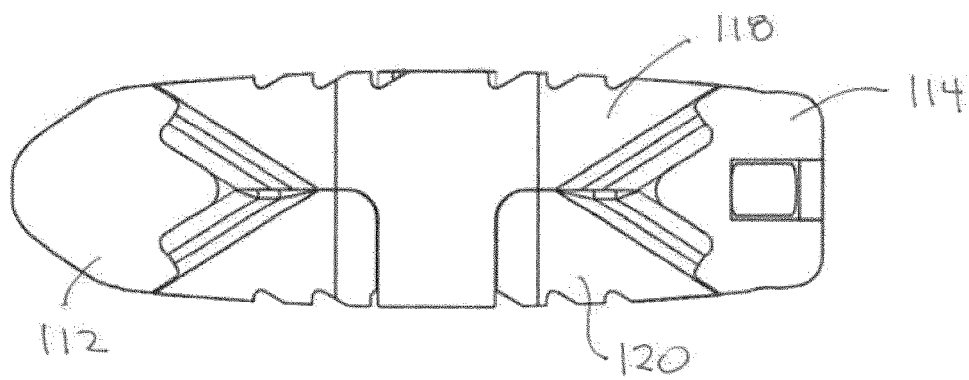
Figure 22:
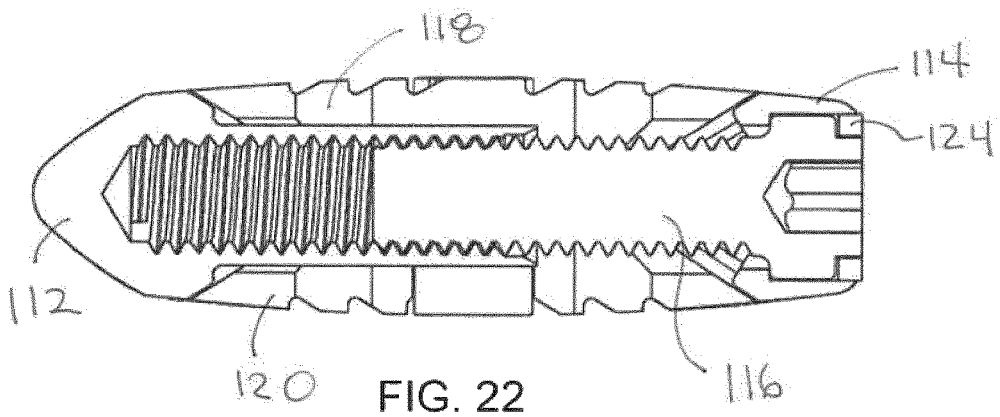
Figure 23:
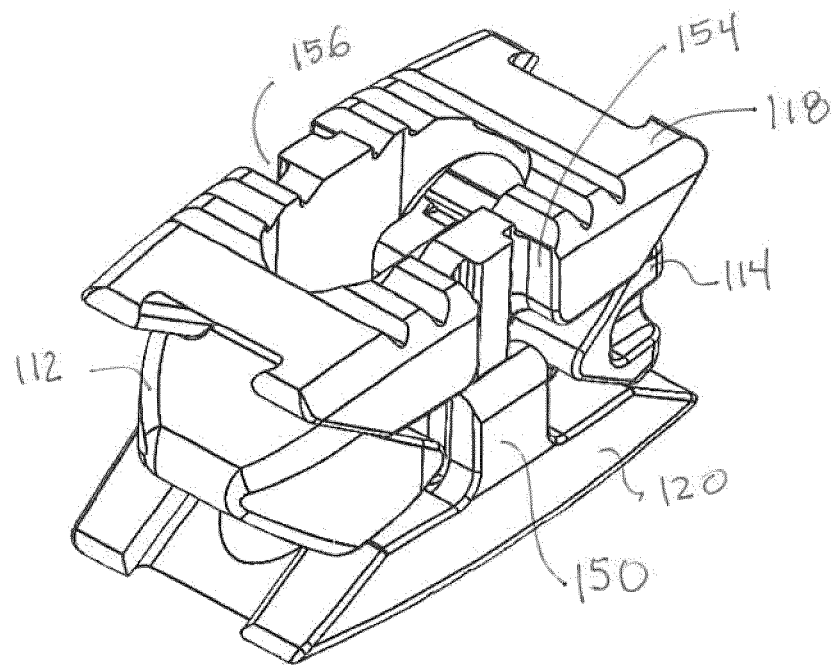
Figure 24:
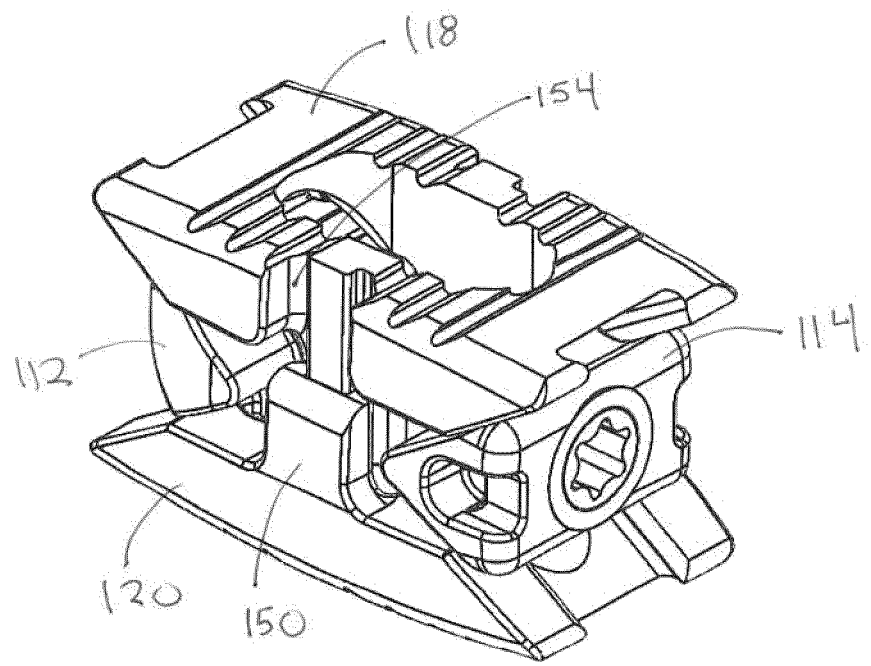
Figure 25:
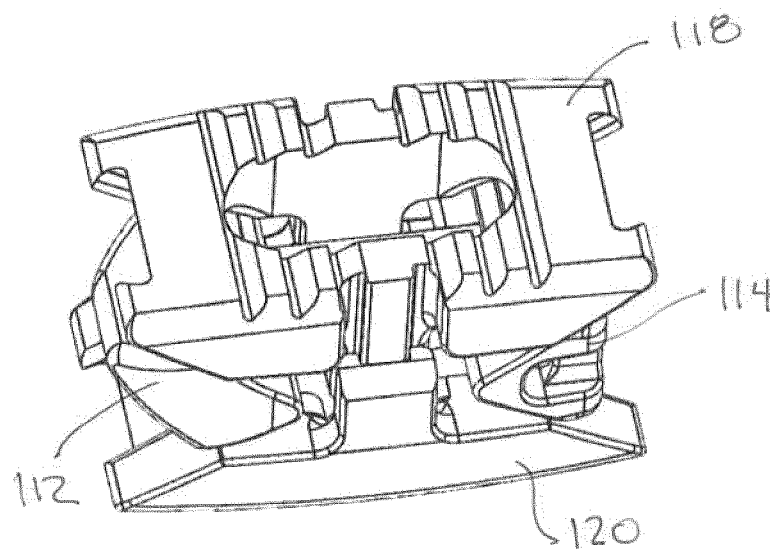
Figure 26:
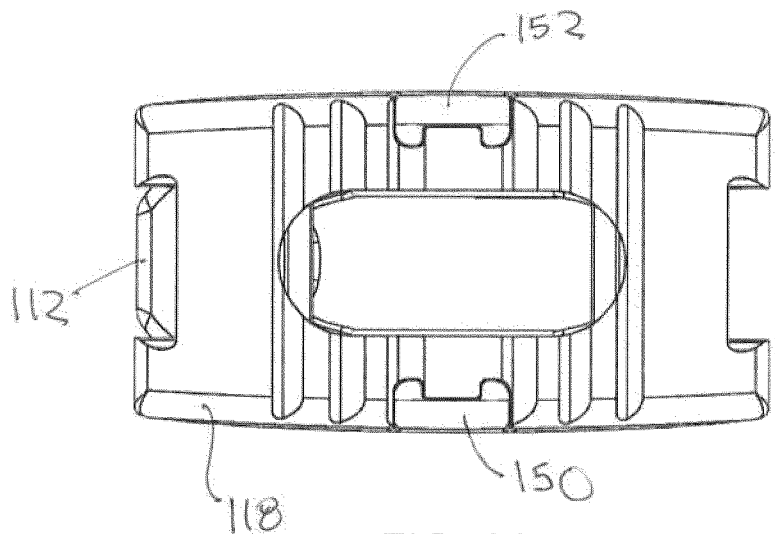
Figure 27:
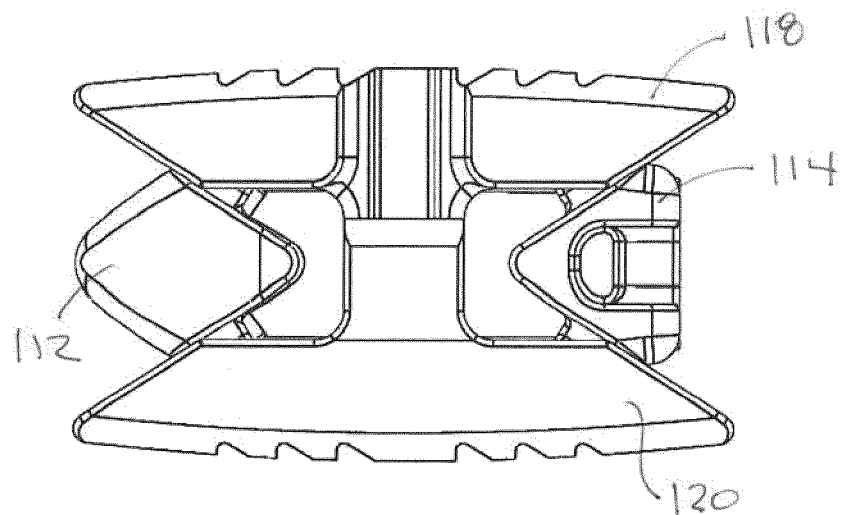
Figure 28:
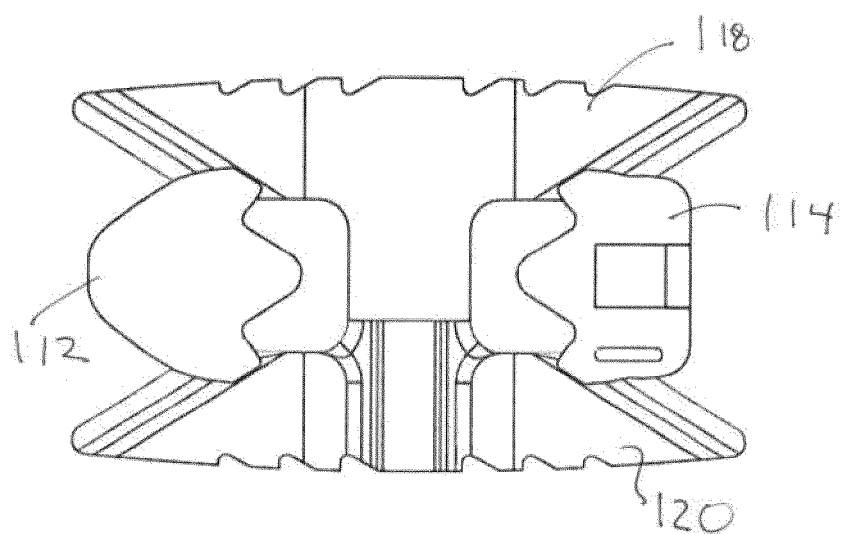
Figure 29:
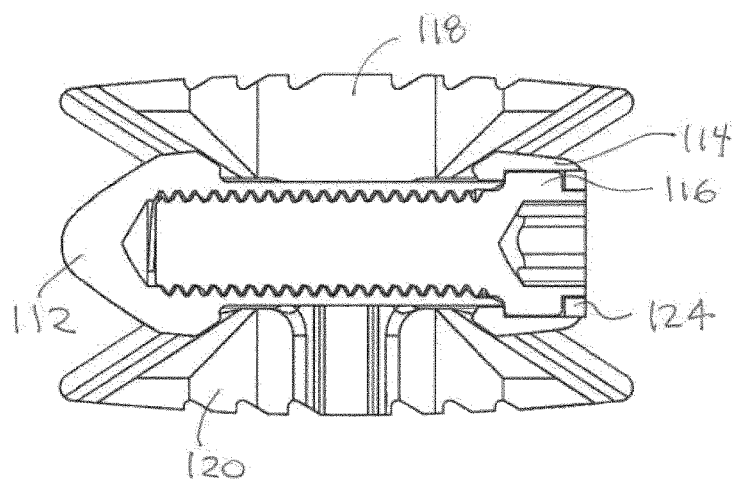
Figure 30:
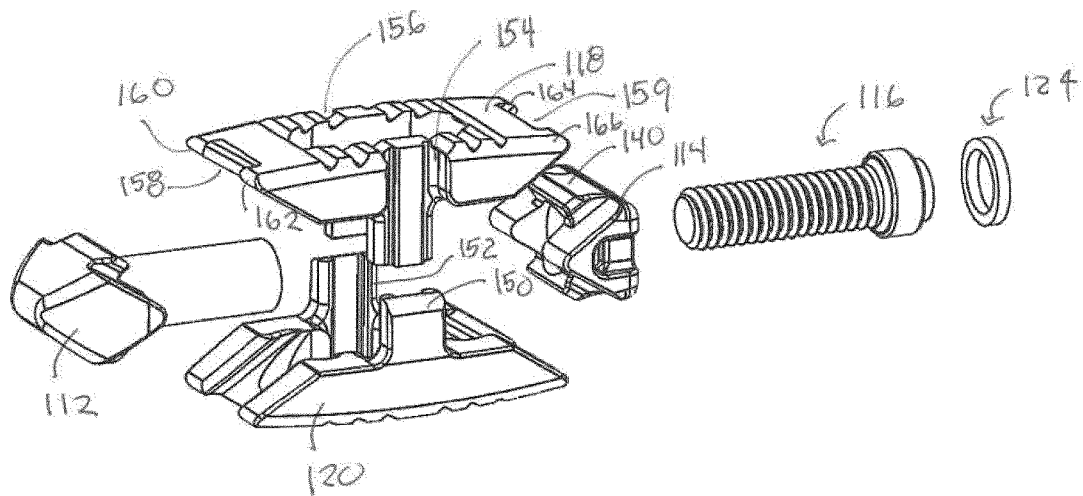
Figures 31, 32:
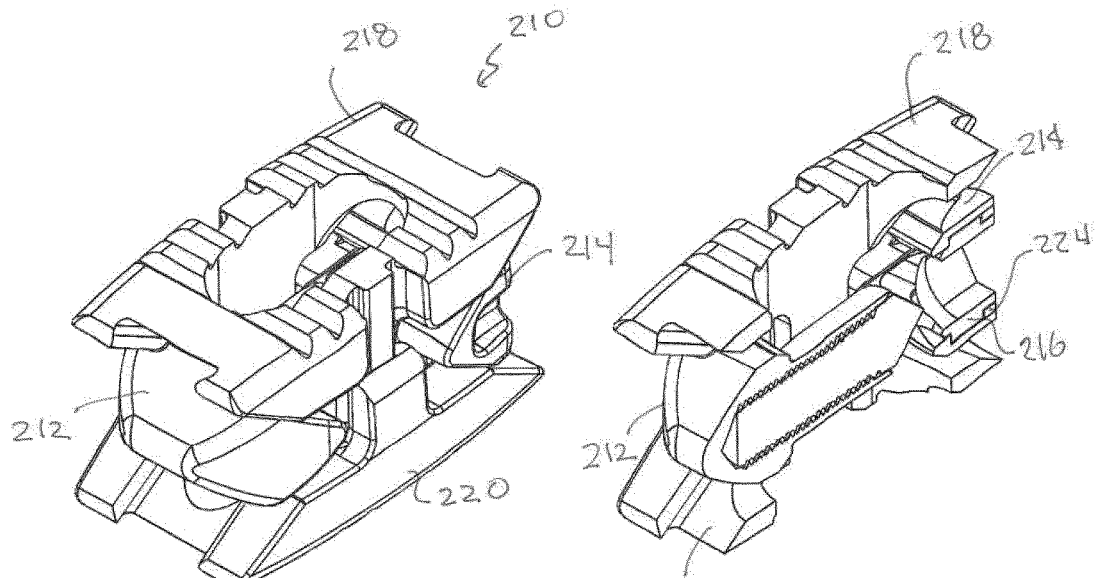
FIGS. 31-38 show various views of an expandable implant according to an alternative embodiment.
Figure 33:
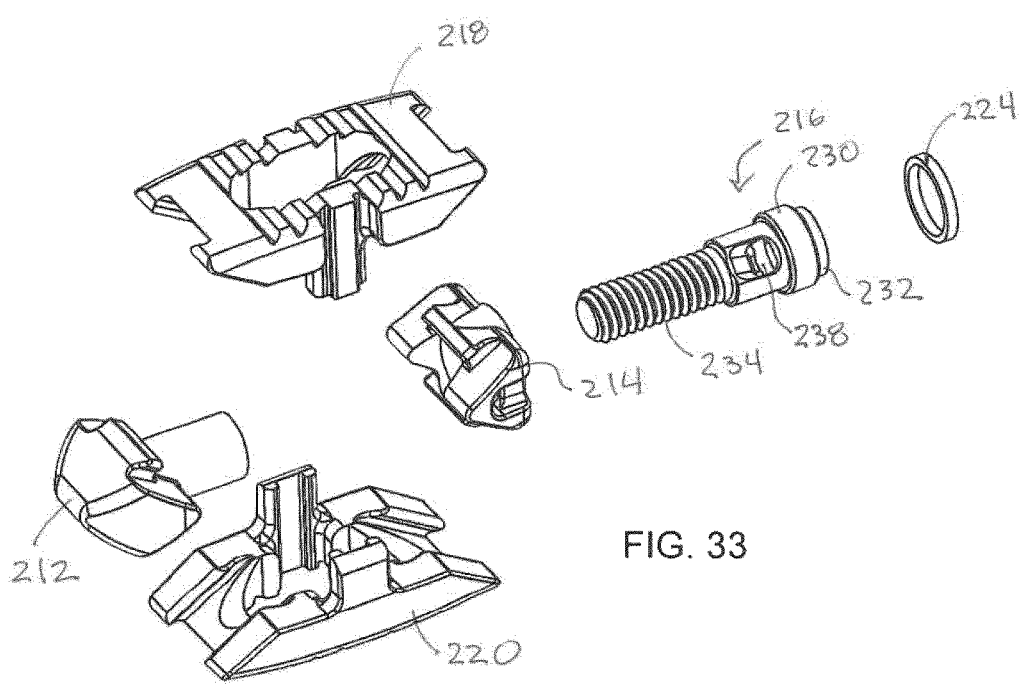
Figure 34:
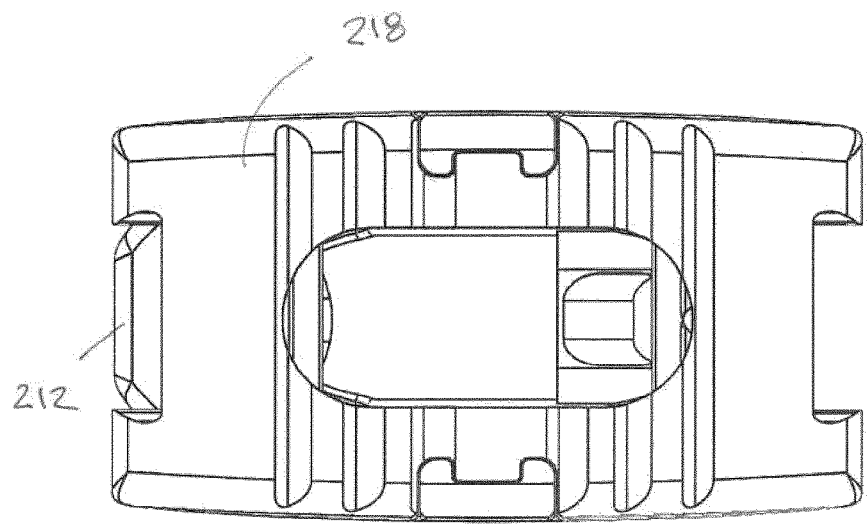
Figures 35, 36:
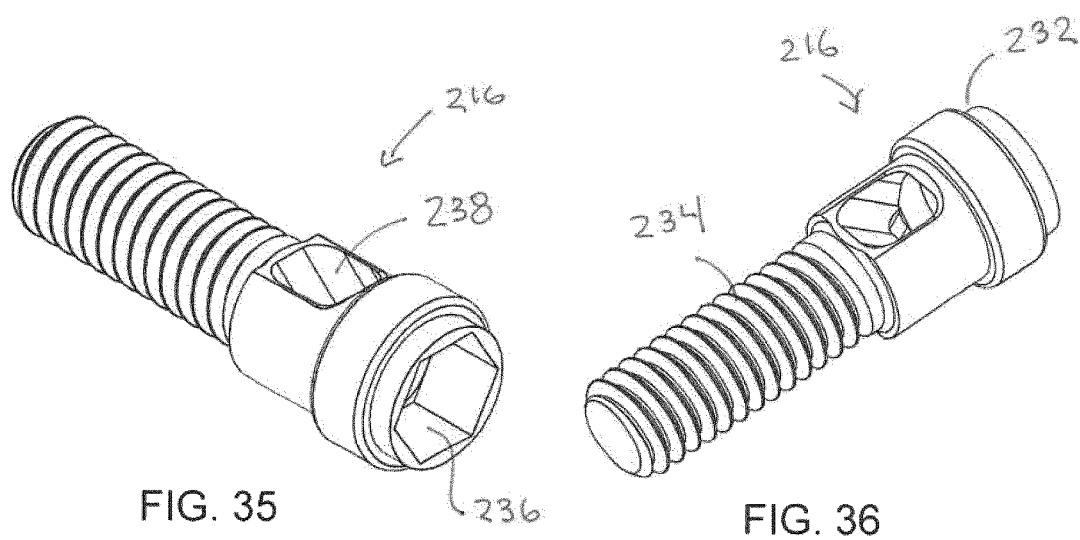
Figure 37:
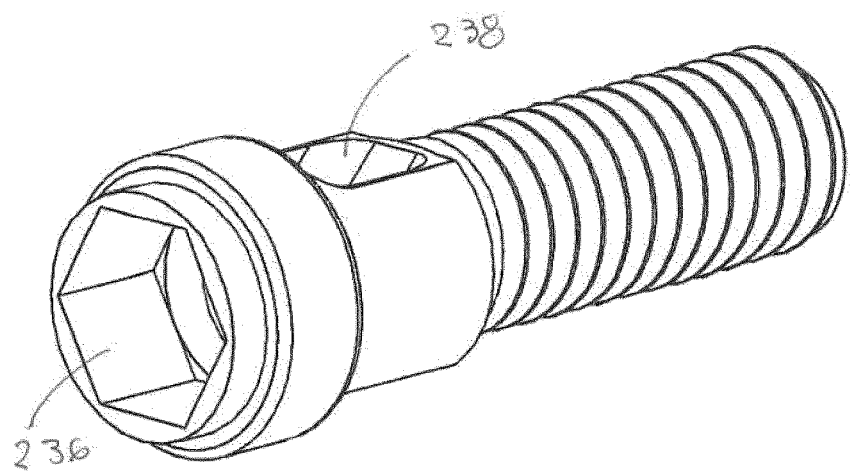
Figure 38:
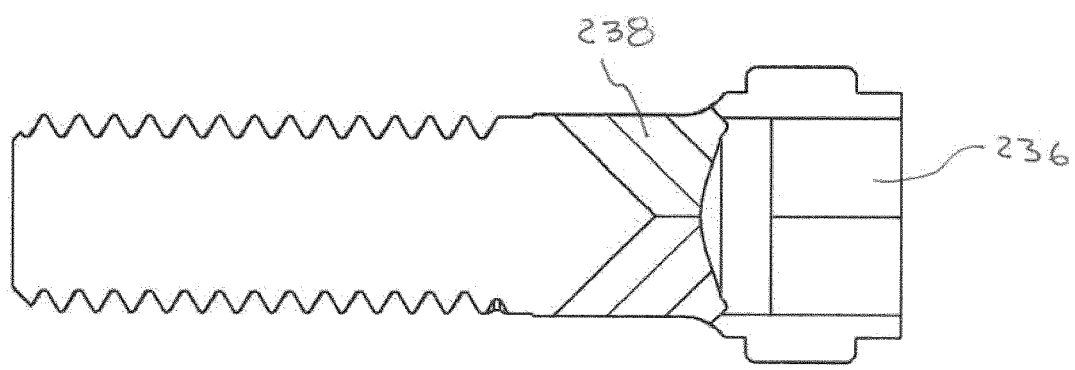
Figure 39:
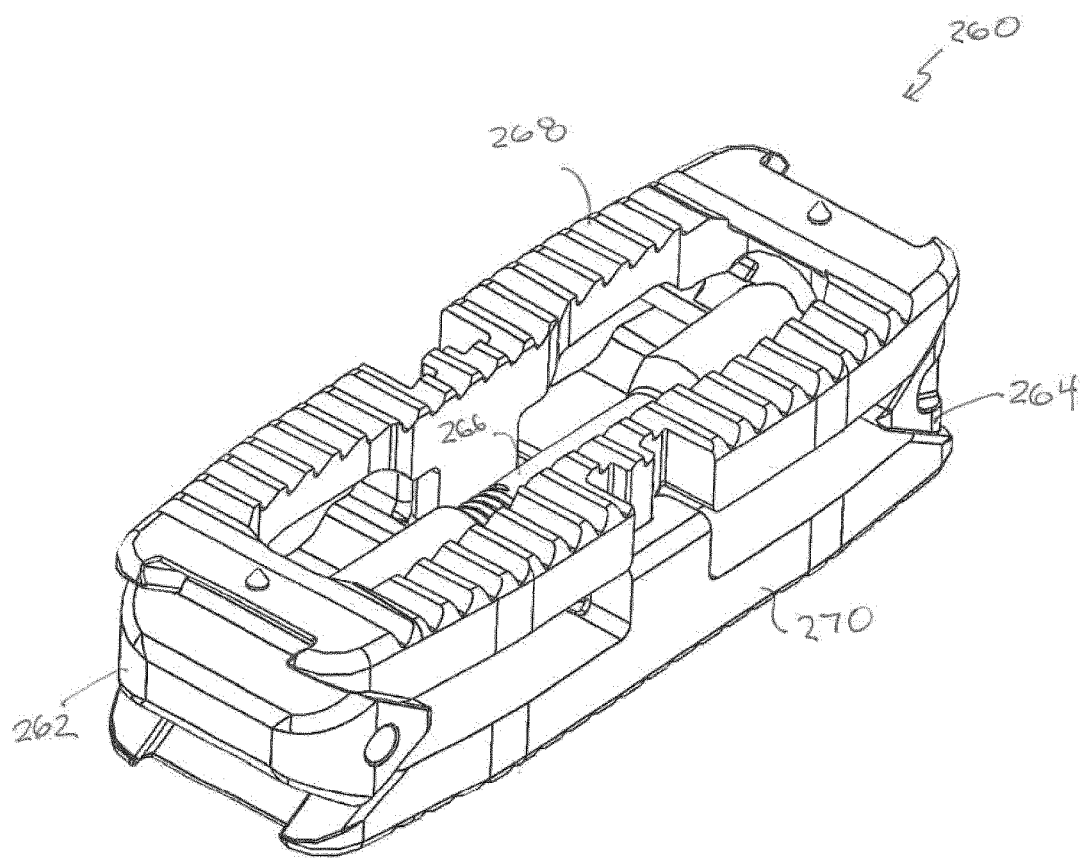
FIGS. 39-46 show various views of an expandable implant according to an alternative embodiment.
Figure 40:
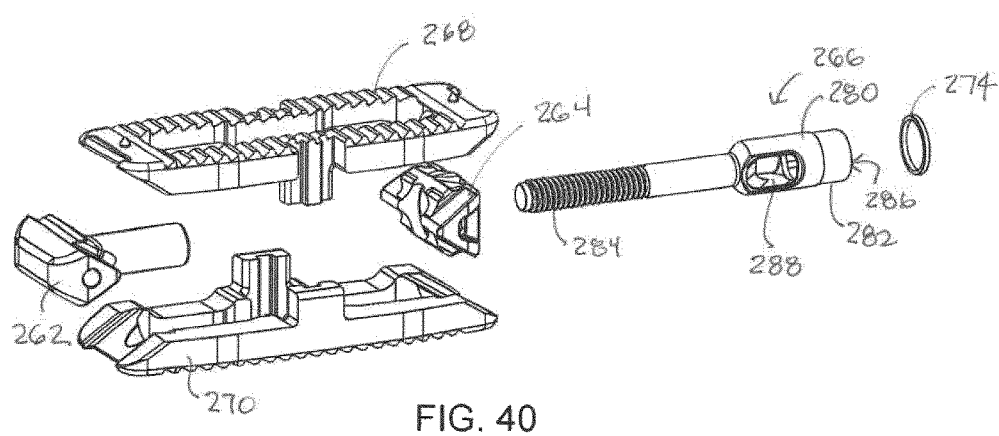
Figure 41:
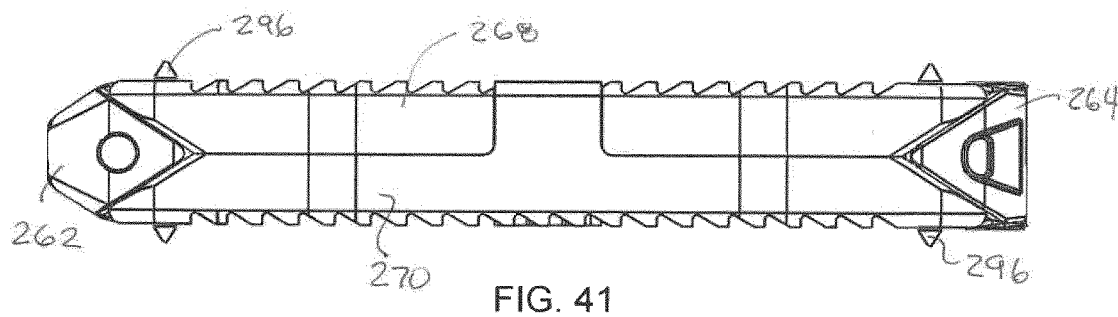

As shown in FIGS. 20-22, the ramped surfaces extend at an angle relative to axis 111, and the projections extend upward/downward relative to the ramped surfaces. The ramped surfaces are generally flat surfaces configured to engage a correspondingly ramped surface on first support 118. The projections extend laterally across front portion 112. In some embodiments, the projections may have a dovetail shape, while in other embodiments, the projections may take other shapes, including having an undercut portion, etc. The dovetail shape provides a relatively larger top portion and an undercut lower portion such that front portion 112 and first support 118 can slide relative to one another, but the parts cannot be separated, for example, by merely lifting first support 118 away from front portion 112 (e.g., in an upward direction generally perpendicular to axis 111). It should be noted that similar to implant 10, implant 110 includes front and rear, upper and lower ramped surfaces and projections configured to provide the interface between front and rear portions 112, 114 and first and second supports 118, 120.

As with implant 10, according to an exemplary embodiment, first and second supports 118, 120 and front and rear portions 112, 114 have corresponding geometric features (e.g., correspondingly ramped surfaces) such that displacement of front portion 112 relative to rear portion 114 along axis 111 causes relative planar and/or linear displacement of first and second supports 118, 120. As discussed above, the geometric features of the various components may be varied to provide for varying adjustment features for first and second supports 118, 120.

In use, control member 116 includes a head portion and a body portion and extends through a through-hole in rear portion 114 and into front portion 112. The head portion of control member 116 seats in a counterbore of rear portion 114, and the threaded portion of the body threadingly engages an aperture of front portion 112. The head portion may include an annular recess (similar to head portion 106 of implant 10) configured such that a collar 124 can be positioned (e.g., press-fit, welded, etc.) into the counterbore rearward of the head portion to retain control member 116 in place. As a user rotates control member 116, front portion 112 and rear portion 114 move toward/away from each other (depending on the direction of rotation), and first and second supports 118, 120 in turn move away from/toward each other. While the Figures generally show control member 116 threadingly engaging front portion 112, in other embodiments, other adjustment mechanisms may be used (e.g., ratchet mechanisms, indents/detents, etc.).

Opposing projections 160, 162 on first support 118 form a recess, or channel 158. In one embodiment, channel 158 has a dovetail shape corresponding in shape to projection 130 on front portion 112. Likewise, projections 164, 166 in first support 118 form channel 159 having a dovetail shape similar in shape to projection 140 on rear portion 114. Projections 130, 140 slide within channels 158, 159 as first support 118 moves up/down. In some embodiments, retaining members or pins (e.g., similar to pins 22) extend through first and second supports 118, 120 and act to limit the range of movement of first and second supports 118, 120 relative to front and rear portions 112, 114, and prevent first and second supports 118, 120 from being completely removed from front and rear portions 112, 114. Second support 120 includes similar features such as an outer, or bottom surface, ramped surfaces, channels, and two pairs of opposing projections.

Figure 16:
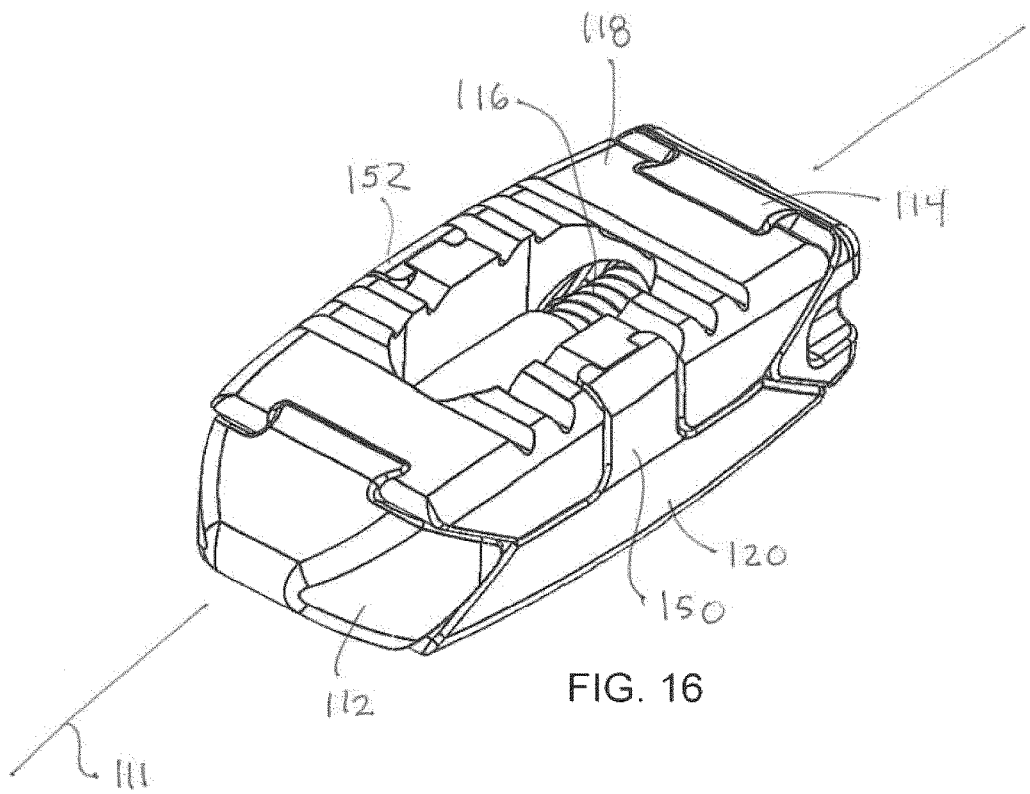
FIGS. 16-30 show various views of an expandable implant according to an alternative embodiment.
Figure 17:
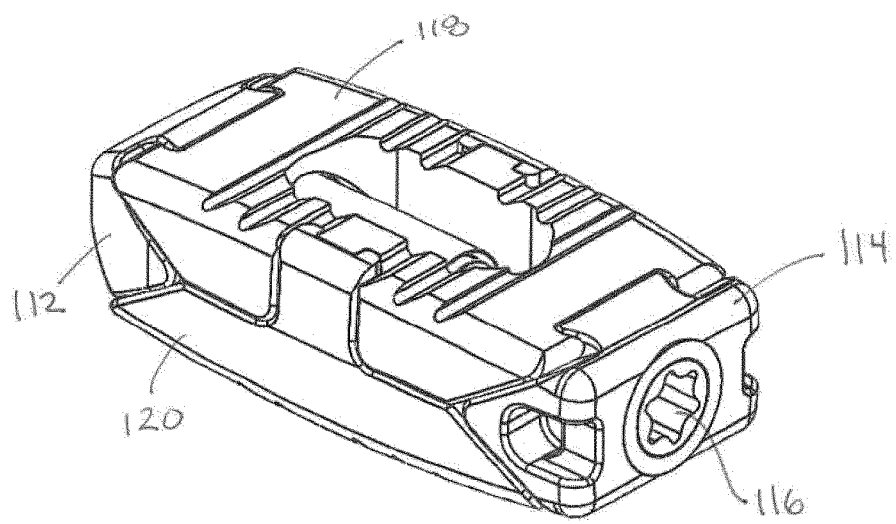
Figure 18:
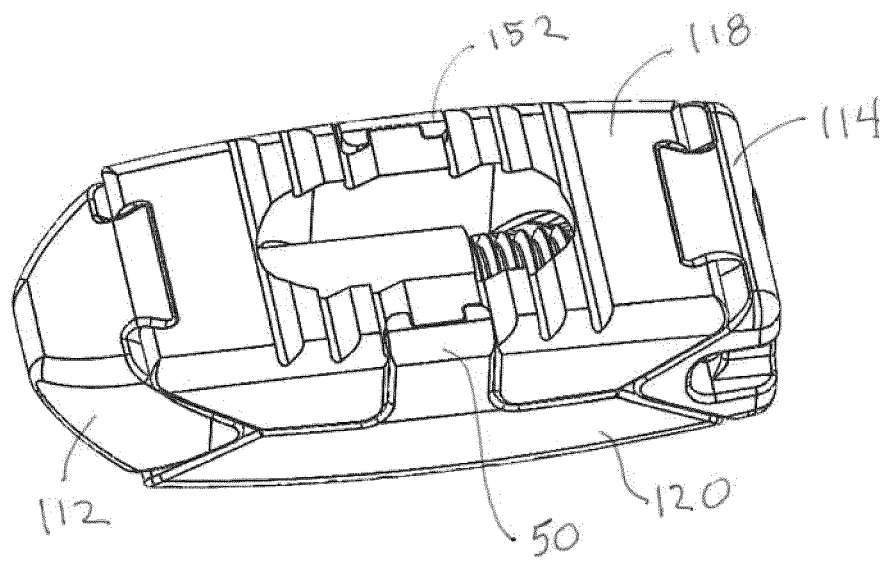
Figure 19:
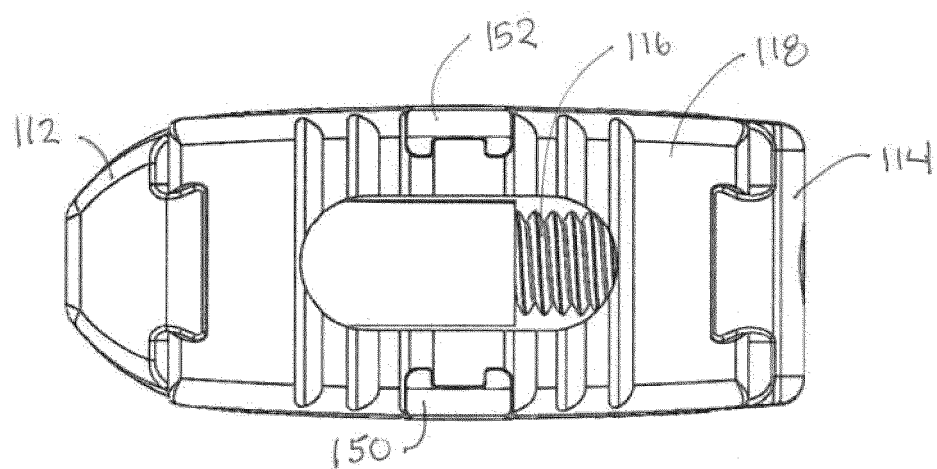

In addition to including various features of implant 10, implant 110 further includes an alignment feature intended to maintain alignment between first and second supports 118, 120 during use. In one embodiment, second support 120 includes one or more alignment members 150, 152 (e.g., extensions, projections, etc.) that extend generally upward as shown in FIG. 19 (e.g., in a direction generally perpendicular to axis 111). Members 150, 152 are received in recesses 154, 156 (e.g., channels, grooves, slots, etc.), respectively, formed in first support 118. Members 150, 152 and recesses 154, 156 have corresponding geometric features to ensure a snug fit between components. For example, as shown in FIG. 16, members 150, 152 are generally U-shaped in cross-section, and recesses 154, 156 are shaped to receive the U-shaped members. The alignment features prevent relative "rocking" of the supports, and in some embodiments serve to maintain a generally parallel relationship between the supports. In some embodiments, spaces or gaps may be provided between members 150, 152 and recesses 154, 156 to enable a predetermined amount of angular offset between the supports.

In one embodiment members 150, 152 are formed so as to be generally flush with the exterior surface of first support 118 (e.g., along a side or top surface). In other embodiments, members 150 may be recessed from, or alternatively protrude beyond, the exterior surface of first support 118. Further, while FIGS. 16-30 show two alignment members 150, 152, in various alternative embodiments fewer or more alignment members and/or recesses may be utilized (e.g., 1, 3, 4, etc.). Further yet, members 150, 152 may be integrally formed with, or removably coupled to, a remainder portion of second support 120. In further embodiments, the relative positions of alignment members 150, 152 and recesses 154, 156 are reversed (e.g., such that members 150, 152 are provided on first support 118 and recesses 154, 156 are provided on second support 120). Other variations in the size, number, and placement of members 150, 152 and recesses 154, 156 may be made according to various embodiments.

It should be noted that implant 110 may share various features with the other implants described herein, and be made of the same, similar, or different materials. For example, various components of implant 110 may be made of metal, plastic, composites, or other suitable bio-compatible materials. Further, implant 110 may be usable in connection with the spine or other parts of the body. Further yet, pins similar to pins 22 may be used in conjunction with implant 110 or any of the other implants shown and described herein.

In various embodiments, the implants shown in FIGS. 1-15 and 16-30 share various common features. For example, the control member or screw (e.g., 16, 116) is contained within the device, such that neither end of the control member or screw protrudes past the end members. For example, as shown in FIG. 14, the control member 16 may be received by or through rear portion 14 in a counterbore and held captive by collar or ring 24, such that control member 16 is free to rotate within rear portion 14, but does not threadingly engage rear portion 14. As such, rear portion 14 remains fixed relative to control member 16 as control member 16 is rotated. Control member 16 threadingly engages a threaded aperture 34 defined by a boss extending rearward from front portion 12, such that as control member 16 rotates, front portion 12 moves relative to control member 16 (e.g., control member 16 moves into or out of the threaded boss of front portion 12). As such, control member 16 is contained entirely within the periphery of front and rear portions 12, 14. The control member 16 may in some embodiments be configured to be flush with the outer sides of front and rear portions 12, 14. In other embodiments, the control member 16 is recessed within front and/or rear portions 12, 14. For example, as shown in FIG. 14, front portion 12 has a solid, bull-nose configuration such that control member 16 is concealed therein. In various embodiments, the implants include grooves that may help secure the implant in the body of a patient, by providing spaces for structures in the body of a patient to engage the grooves.

Referring now to FIGS. 31-38, an implant 210 is shown according to an exemplary embodiment. Implant 210 is usable, for example, between and/or within vertebral bodies of the spine, and may share many of the features of the other inter/intra-body implants discussed elsewhere herein. It should be understood that implant 210 may in some embodiments be usable in other portions of the body in addition to the spine, and all such applications are to be understood to be within the scope of the present disclosure. Implant 210 is generally similar to implants 10 and 110 in structure and function except with respect to the additional access port features discussed below. As such, implant 210 is understood to include any or all of the features of implants 10 and 110 to the extent consistent with the additional features of implant 210 described herein (e.g., retention pins, dovetail projections and ramped surfaces, alignment features, etc.).

According to an exemplary embodiment, implant 210 includes a first, or front portion 212, a second, or rear portion 214, and a third, intermediate, or control member or portion 216, which collectively form a body or control assembly that extends along a longitudinal axis of implant 210. A first, or upper support 218 (e.g., an upper plate or support member, etc.) and a second, lower support 220 (e.g., a lower plate or support member), are coupled to the body assembly and may extend generally between front and rear portions 212, 214. According to an exemplary embodiment, first and second supports 218, 220 define a height of implant 210 extending between the outer or top surface of first support 218 and the outer or lower surface of second support 220.

In one embodiment, control member 216 includes a head portion 230, a collar recess 232, a threaded portion 234, a tool recess 236, and access ports 238. Threaded portion 234 and the non-threaded portion of control member 216 including access ports 238 collectively form a body portion for control member 216. Head portion 230 is received within a counterbore in rear portion 214. Collar recess 232 is configured to enable placement of collar 224 into a position to retain head portion 230 within the counterbore in rear portion 214. Threaded portion 234 is configured to threadingly engage a threaded aperture provided by front portion 212. Tool recess 236 is formed in the rearward portion of head portion 230 and communicates with access ports 238, which extend to opposite sides of control member 216. Tool recess 236 is configured to receive a tool to enable threading manipulation of control member 216. Tool recess 236 and access ports 238 are collectively configured to provide a fluid path to an interior of implant 210 and enable delivery of fluid, bone growth material, or other material to an interior of implant 210.

As shown in FIGS. 35-38, in one embodiment, two access ports 238 are in communication with tool recess 236 and extend to opposite sides of control member 216. In other embodiments, more or fewer access ports 238 may be utilized, and the size and shape of the individual access ports 238 may be varied to suit a particular application, size of implant, and the like. Access ports 238 are positioned to provide fluid communication with an interior area of implant 210.

Referring to FIGS. 39-46, an implant 260 is shown according to an exemplary embodiment. Implant 260 is usable, for example, between and/or within vertebral bodies of the spine, and may share many of the features of the other inter/intra-body implants discussed elsewhere herein. It should be understood that implant 260 may in some embodiments be usable in other portions of the body in addition to the spine, and all such applications are to be understood to be within the scope of the present disclosure. Implant 260 is generally similar to implants 10, 110, and 210 (and the other implants described herein) in structure and function except with respect to the additional conical projection, side bone graft window, and elongated component features discussed below. As such, implant 260 is understood to include any or all of the features of the other implants described herein to the extent consistent with the additional features of implant 260 described herein (e.g., retention pins, dovetail projections and ramped surfaces, alignment features, control member access port(s), etc.).

According to an exemplary embodiment, implant 260 includes a first, or front portion 262, a second, or rear portion 264, and a third, intermediate, or control member or portion 266, which collectively form a body or control assembly that extends along a longitudinal axis of implant 260. A first, or upper support 268 (e.g., an upper plate or support member, etc.) and a second, lower support 270 (e.g., a lower plate or support member), are coupled to the body assembly and may extend generally between front and rear portions 262, 264. According to an exemplary embodiment, first and second supports 268, 270 define a height of implant 260 extending between the outer or top surface of first support 268 and the outer or lower surface of second support 270.

In one embodiment, control member 266 includes a head portion 280, a collar recess 282, a threaded portion 284, a tool recess 286, and access ports 288. Head portion 280 is received within a counterbore in rear portion 264. Collar recess 282 is configured to enable placement of collar 274 into a position to retain head portion 280 within the counterbore of rear portion 264. Threaded portion 284 is configured to threadingly engage a threaded aperture provided by front portion 262. Tool recess 286 is formed in the rearward portion of head portion 280 and communicates with access ports 288, which extend to opposite sides of control member 266. Tool recess 286 is configured to receive a tool to enable threading manipulation of control member 266. Tool recess 286 and access ports 288 are collectively configured to provide a fluid path to an interior of implant 260 and enable delivery of fluid, bone growth material, or other material to an interior of implant 260.

Figure 45:
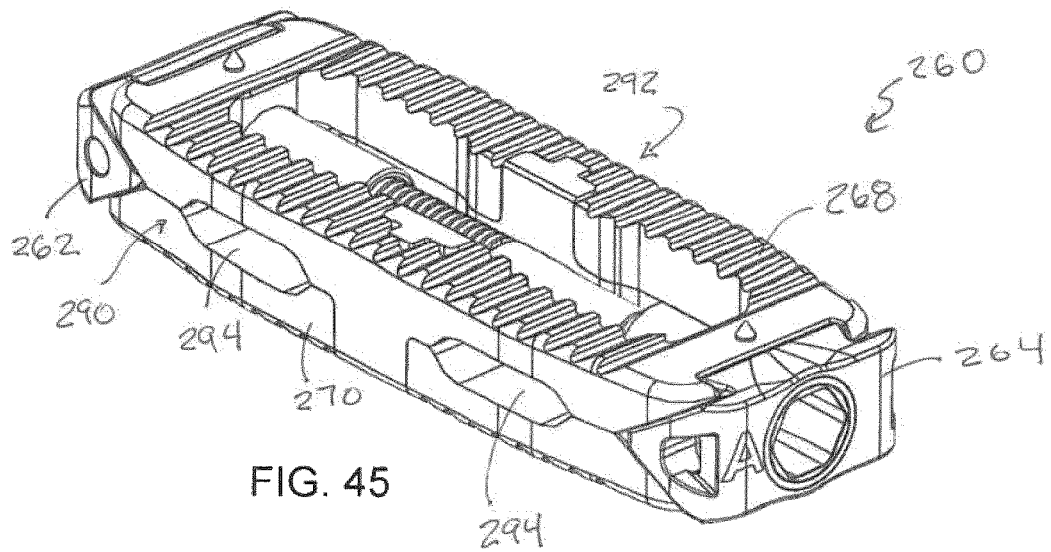
Figure 46:
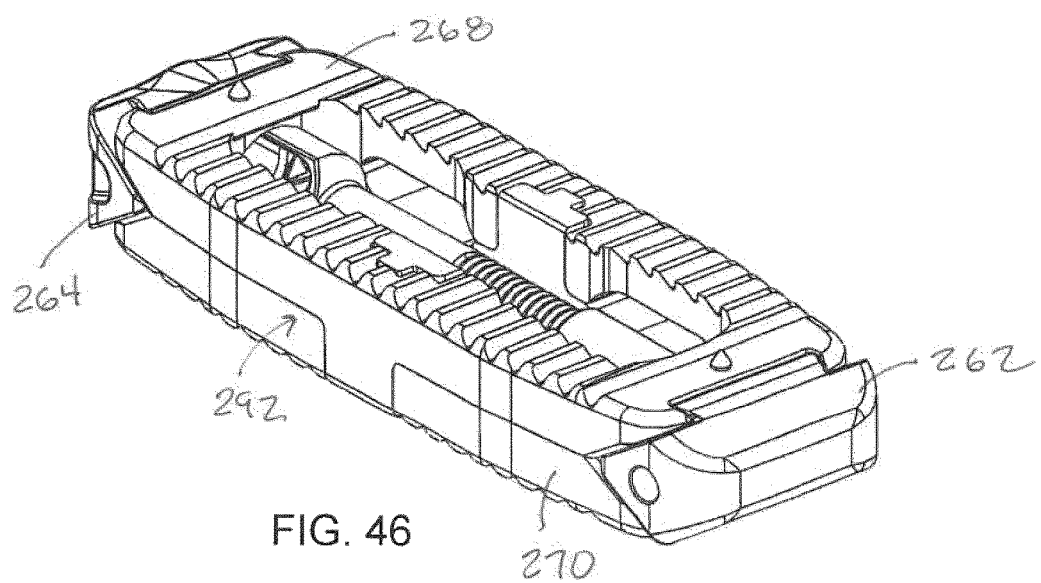

Referring to FIGS. 45-46, in one embodiment implant 260 defines a first side 290 and a second, opposite side 292. First and second sides 290, 292 are generally formed by the sidewalls of top and bottom supports 268, 270. In one embodiment, one or both of first and second sides 290, 292 include side bone graft apertures or windows. For example, as shown in FIG. 45, in some embodiments, first side 290 includes side apertures 294 and second side 292 forms a generally solid sidewall. While FIG. 45 illustrates first side 290 as including two bone graft apertures 294, according to various alternative embodiments, one or both of first side 290 and second side 292 may include more or fewer side apertures. In some embodiments, one or both of top and bottom supports 268, 270 may include a projection 296 (e.g., a conical projection) at one or both ends. Projections 296 may extend above the other portions of top and bottom supports 268, 270 (e.g., teeth, etc.)

Figure 42:
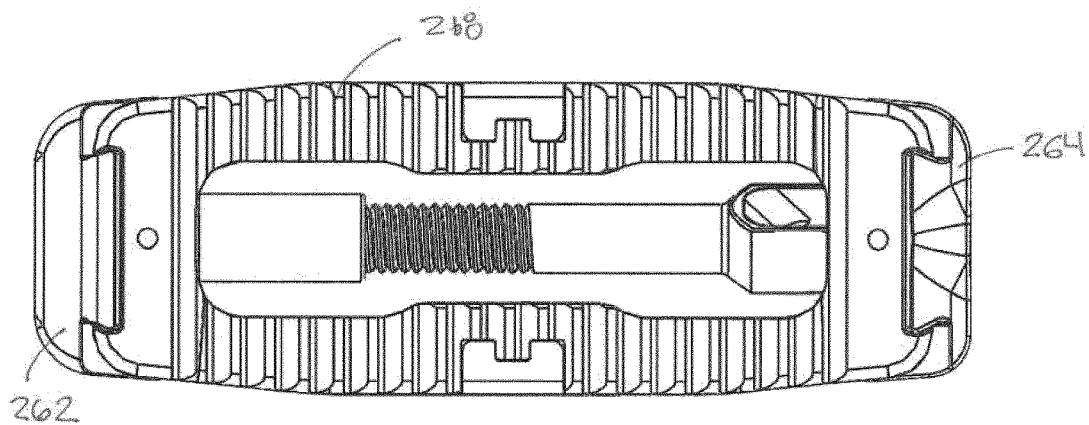
Figure 43:
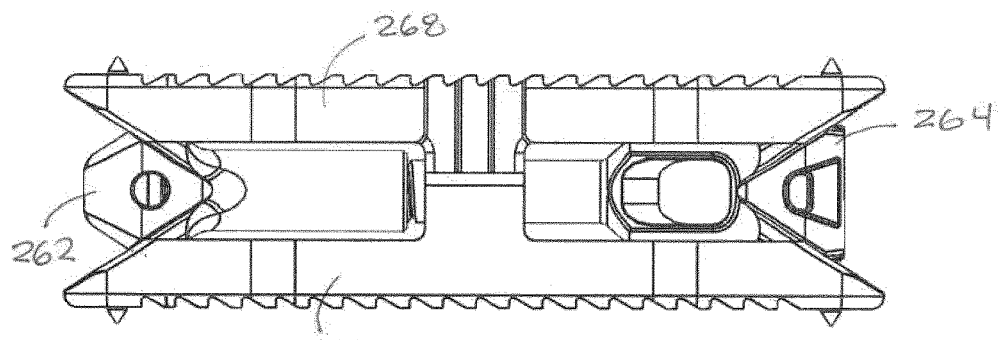
Figure 44:
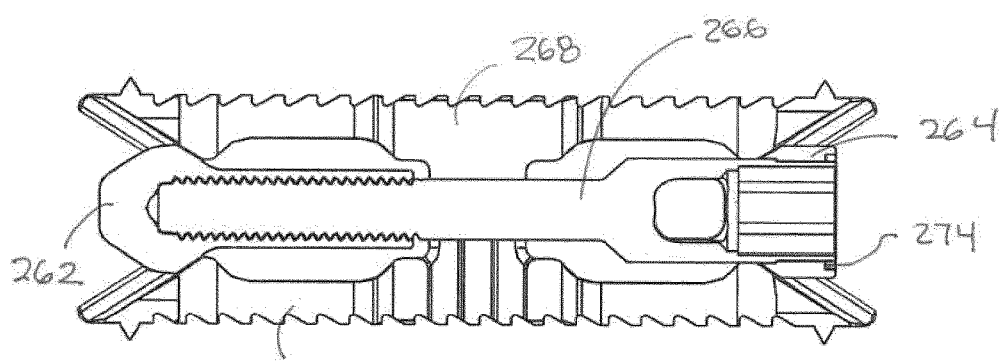

In some embodiments, top and bottom supports 268, 270 have a generally symmetric profile about control member 266, as shown for example, in FIG. 42. Implant 260 may further be elongated relative to other implants illustrated herein, having an overall length to overall width ratio (in the collapsed configuration) of 2, 3, 4, or more (or another ratio, such as a range of between 2 and 5, between 2 and 4, etc.).

Figure 47:
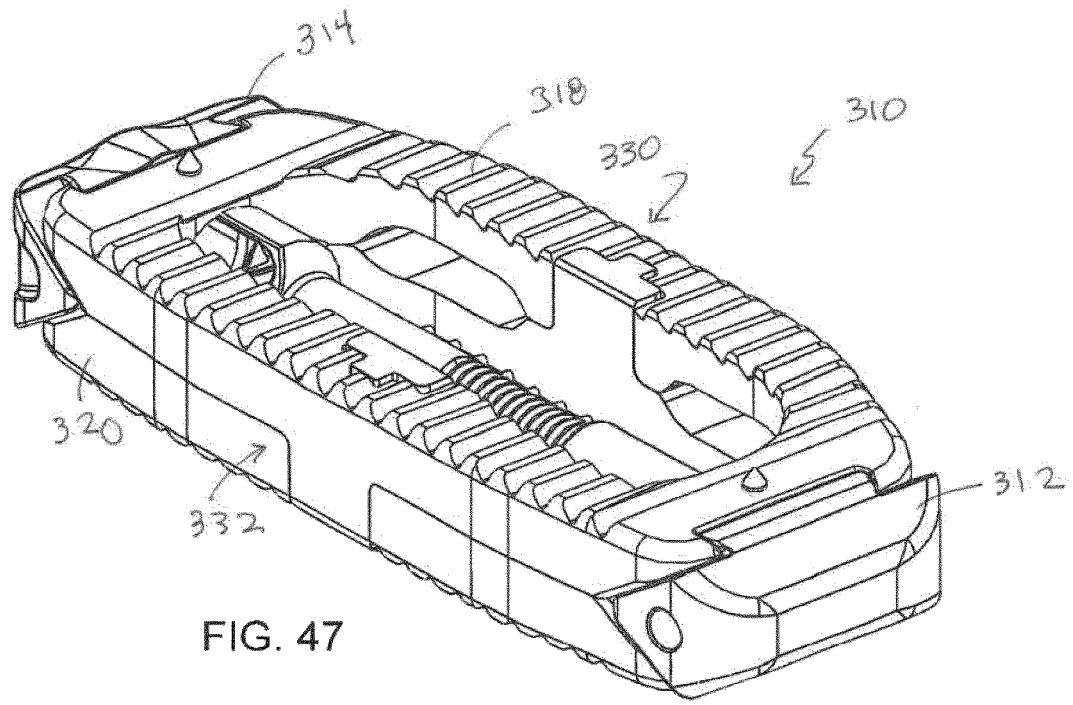
FIGS. 47-49 show various views of an expandable implant according to an alternative embodiment.
Figure 48:
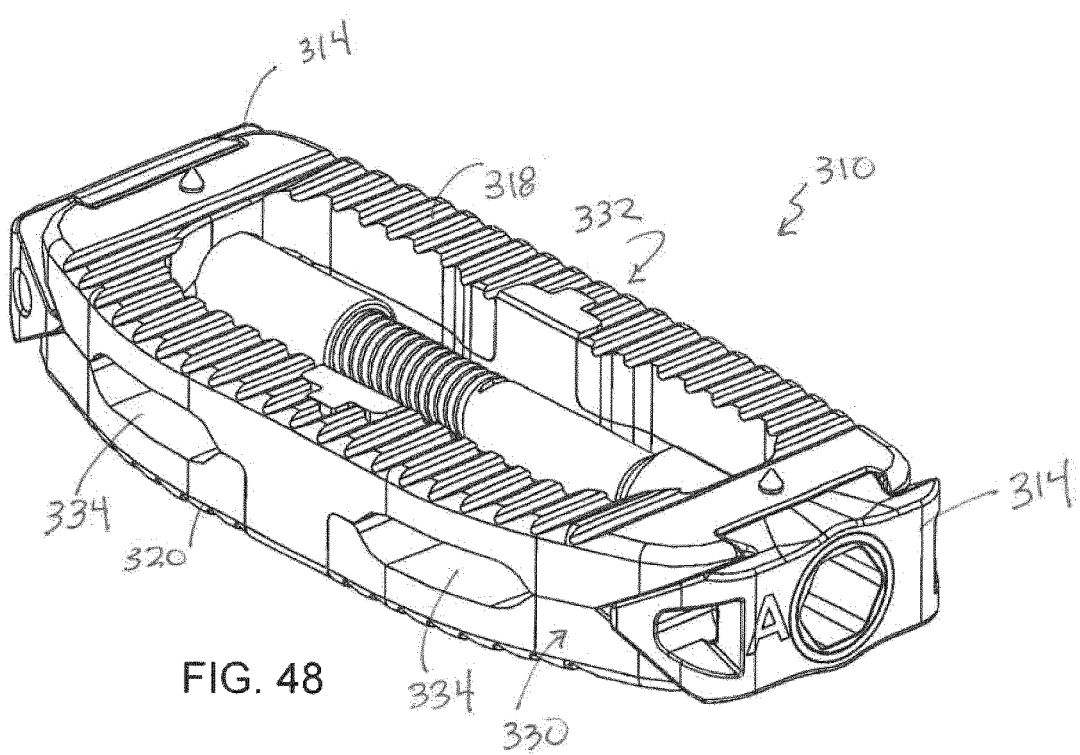
Figure 49:
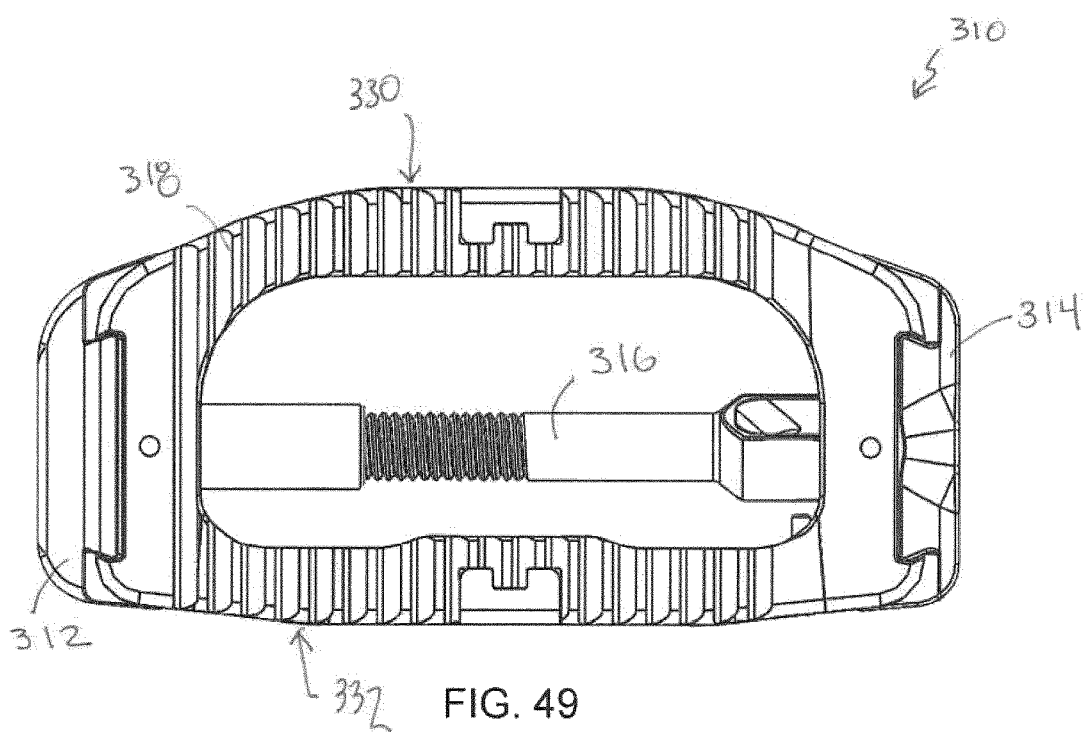

Referring to FIGS. 47-49, an implant 310 is shown according to an exemplary embodiment. Implant 310 is usable, for example, between and/or within vertebral bodies of the spine, and may share many of the features of the other inter/intra-body implants discussed elsewhere herein. It should be understood that implant 310 may in some embodiments be usable in other portions of the body in addition to the spine, and all such applications are to be understood to be within the scope of the present disclosure. Implant 310 is generally similar to implants 260 (and the other implants described herein) in structure and function except with respect to the additional asymmetric component features discussed below. As such, implant 310 is understood to include any or all of the features of the other implants described herein to the extent consistent with the additional features of implant 310 described herein (e.g., retention pins, dovetail projections and ramped surfaces, alignment features, control member access port(s), etc.).

According to an exemplary embodiment, implant 310 includes a first, or front portion 312, a second, or rear portion 314, and a third, intermediate, or control member or portion 316, which collectively form a body or control assembly that extends along a longitudinal axis of implant 310. A first, or upper support 318 (e.g., an upper plate or support member, etc.) and a second, lower support 320 (e.g., a lower plate or support member), are coupled to the body assembly and may extend generally between front and rear portions 312, 314. According to an exemplary embodiment, first and second supports 318, 320 define a height of implant 310 extending between the outer or top surface of first support 318 and the outer or lower surface of second support 320.

In one embodiment, implant 310 defines a first side portion 330 and a second side portion 332. In one embodiment, one or both of first and second side portions 330, 332 include side bone graft apertures or windows. For example, as shown in FIG. 48, in some embodiments, first side 330 includes side apertures 334. While FIG. 48 illustrates first side 330 as including two bone graft apertures 334, according to various alternative embodiments, one or both of first side 330 and second side 332 may include more or fewer side apertures.

In some embodiments, first side portion 330 and second side portion provide an asymmetric profile about control member 316, as shown for example in FIG. 49. In some embodiments, a portion of first side portion 330 extends away from control member 316 a further distance than the corresponding portions of second side portion 332, forming an asymmetric shape (e.g., a "D" or similar shape). Providing an asymmetric profile may provide benefits in particular applications where additional support is desired and/or when placement of implant 310 is difficult. While FIGS. 47-49 shown implant 310 having a general "D" asymmetric shape, according to various alternative embodiments, other asymmetric shapes and configurations may be utilized.

Referring to FIGS. 50-53, an implant 360 is shown according to an exemplary embodiment. Implant 360 is usable, for example, between and/or within vertebral bodies of the spine, and may share many of the features of the other inter/intra-body implants discussed elsewhere herein. It should be understood that implant 360 may in some embodiments be usable in other portions of the body in addition to the spine, and all such applications are to be understood to be within the scope of the present disclosure. Implant 360 is generally similar to implants 260 and 310 (and the other implants described herein) in structure and function except with respect to the additional lateral taper features discussed below. As such, implant 360 is understood to include any or all of the features of the other implants described herein to the extent consistent with the additional features of implant 360 described herein (e.g., retention pins, dovetail projections and ramped surfaces, alignment features, control member access port(s), etc.).

According to an exemplary embodiment, implant 360 includes a first, or front portion 362, a second, or rear portion 364, and a third, intermediate, or control member or portion 366, which collectively form a body or control assembly that extends along a longitudinal axis of implant 360. A first, or upper support 368 (e.g., an upper plate or support member, etc.) and a second, lower support 370 (e.g., a lower plate or support member), are coupled to the body or control assembly and may extend generally between front and rear portions 362, 364. According to an exemplary embodiment, first and second supports 368, 370 define a height of implant 360 extending between the outer or top surface of first support 368 and the outer or lower surface of second support 370. As discuss in greater detail below, the height of implant 360 decreases in a lateral direction.

Figure 50:
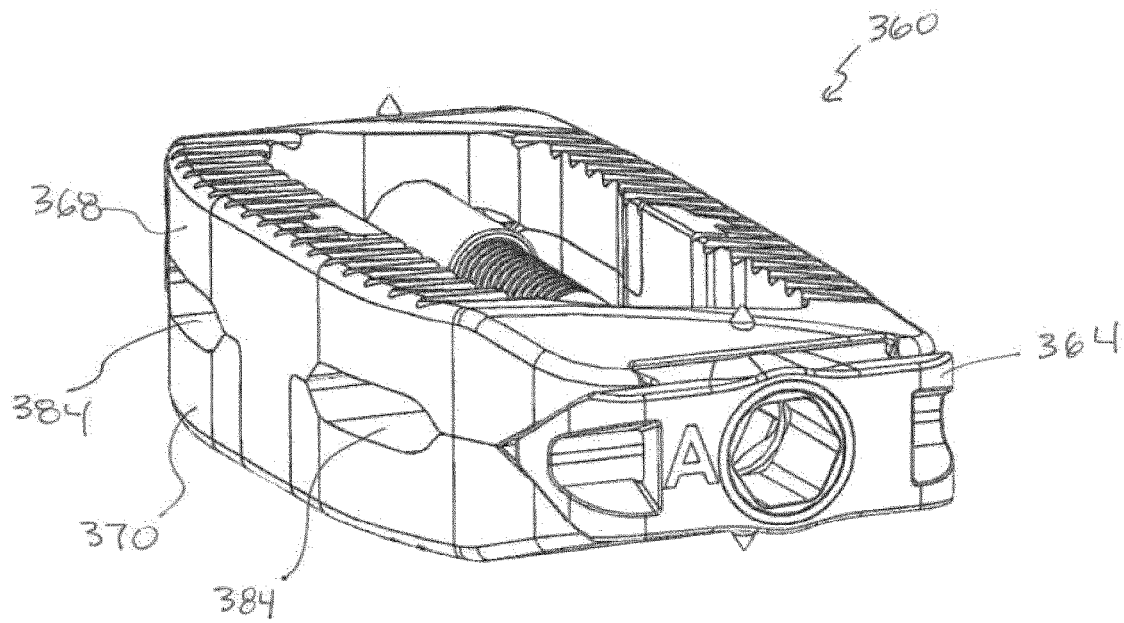
FIGS. 50-53 show various views of an expandable implant according to an alternative embodiment.

In one embodiment, implant 360 defines a first side portion 380 and a second side portion 382. In one embodiment, one or both of first and second side portions 380, 382 include side bone graft apertures or windows. For example, as shown in FIG. 50, in some embodiments, second side 382 includes side apertures 384. While FIG. 50 illustrates second side 382 as including two bone graft apertures 384, according to various alternative embodiments, one or both of first side 380 and second side 382 may include more or fewer side apertures.

Figure 51:
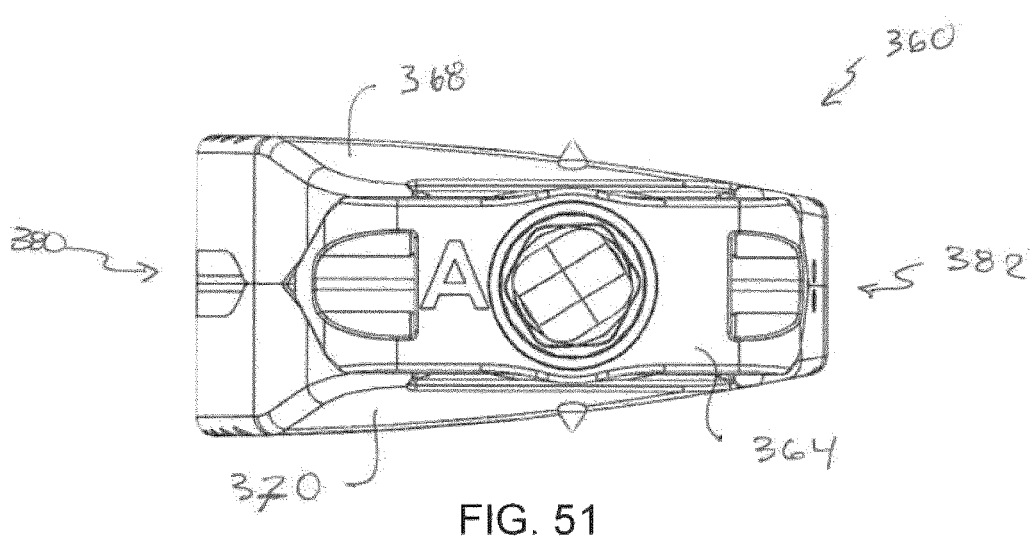
Figure 52:
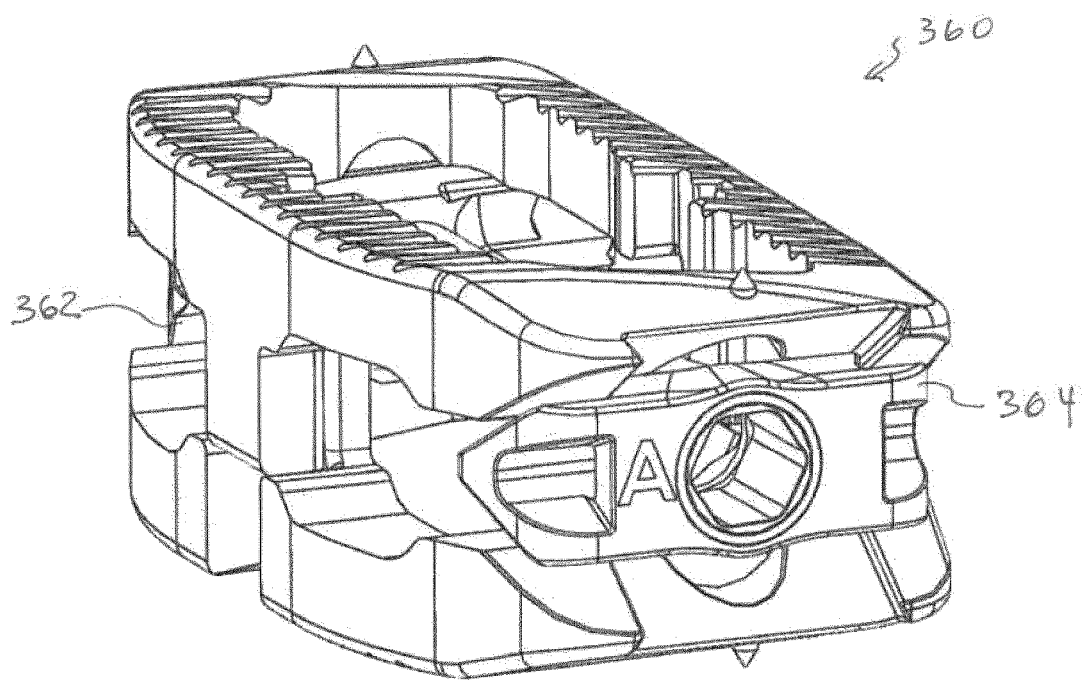
Figure 53:
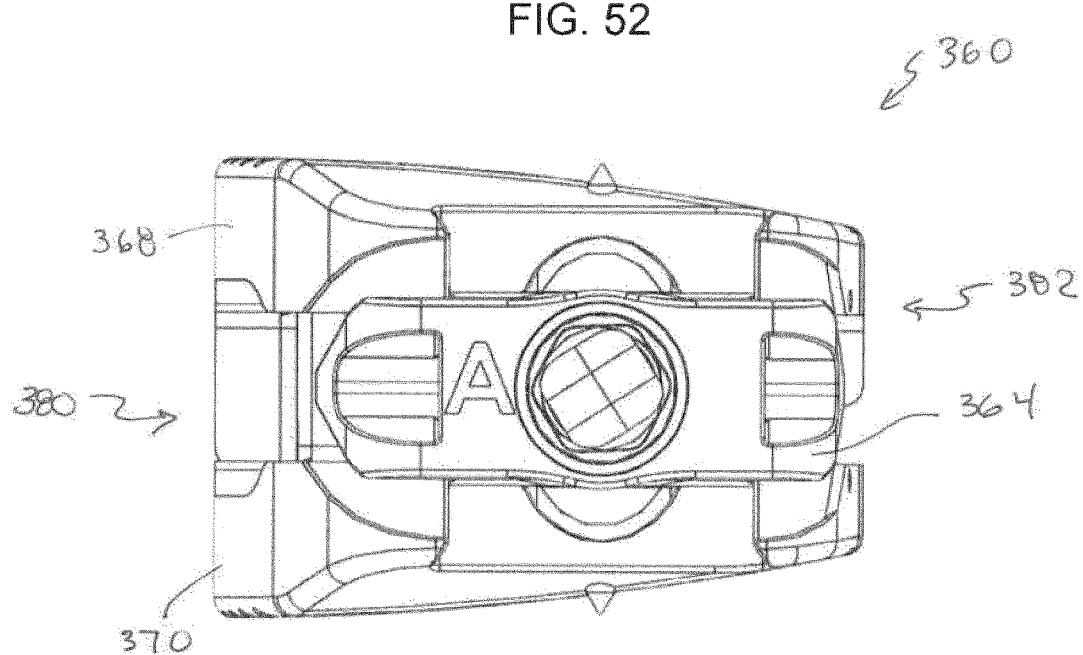
Figure 54:
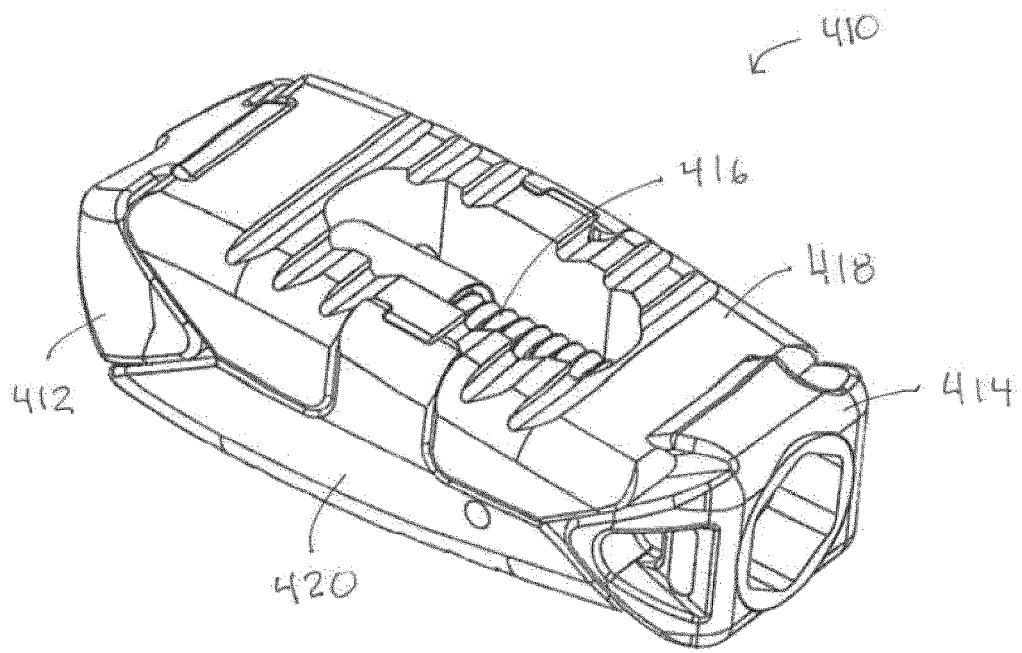
FIGS. 54-65 show various views of an expandable implant according to an alternative embodiment.
Figure 55:
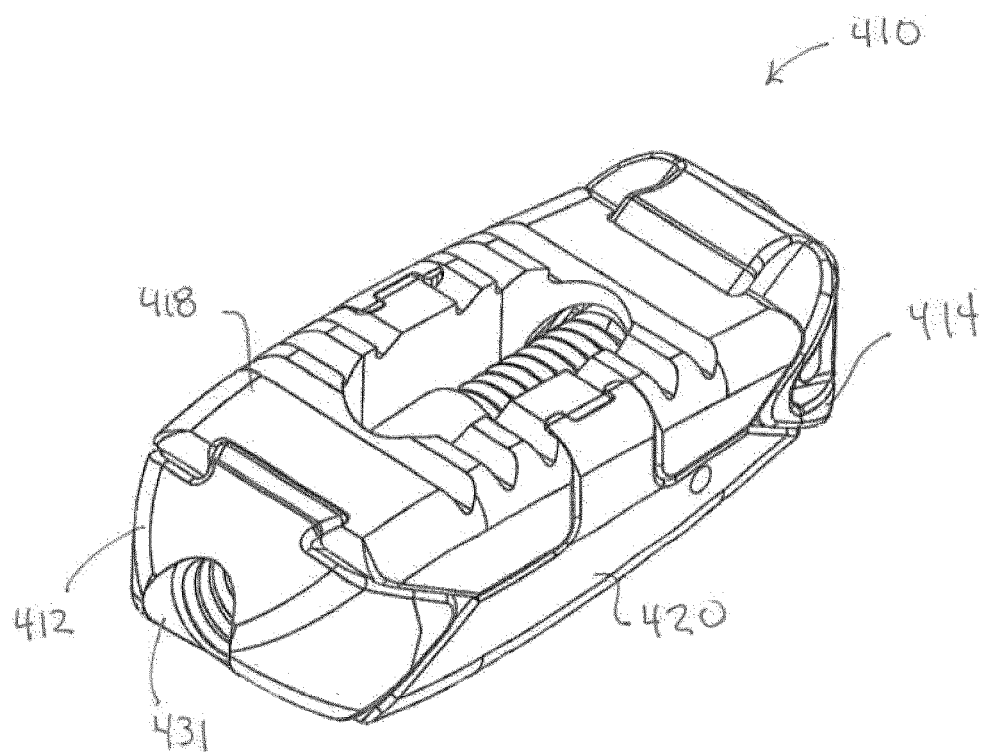
Figure 56:
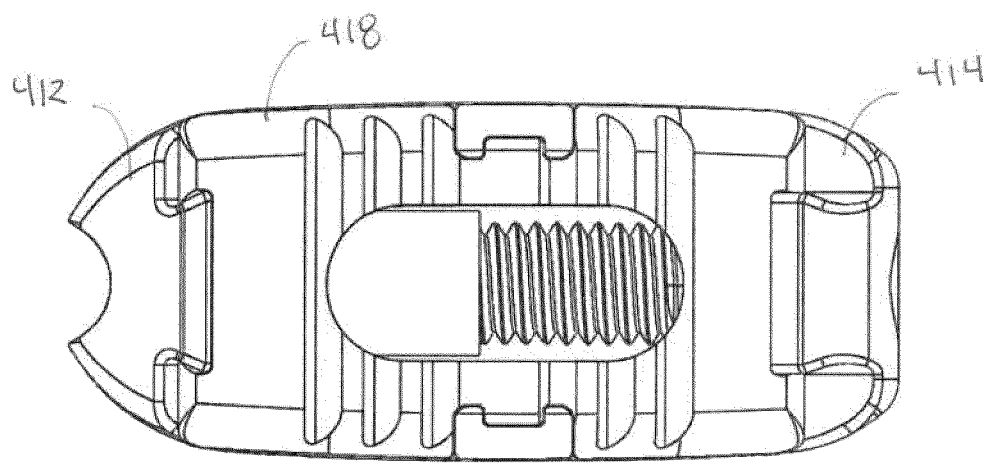

In one embodiment, implant 360 is configured to provide a predetermined lateral taper that remains constant as implant 360 is moved between a collapsed configuration (see FIGS. 50-51) and an expanded configuration (see FIGS. 52-53). For example, referring to FIG. 51, in a collapsed configuration, a first lateral side such as side 380 may have a first height that is larger than a height of second lateral side 382. The degree of taper between the first and second lateral sides 380, 382 may be adjusted to suit a particular embodiment (e.g., a desired spinal curvature). As such, both the top and bottom supports 368, 370 may include outer surfaces (e.g. top and bottom surfaces) that define a lateral angular offset from a parallel configuration (e.g., a configuration where the top and bottom supports 368, 370 are generally parallel).

As shown in FIGS. 51 and 53, top and bottom supports 368 and 370 move toward and away from each other in a linear manner, such that the degree of taper remains constant. In other embodiment, other configurations may be utilized to provide non-linear movement and a varying lateral taper. Furthermore, while FIGS. 50-53 illustrate an implant having a constant lateral taper, according to various alternative embodiments, implants may be provided having a variable longitudinal taper.

Referring to FIGS. 54-65, an implant 410 is shown according to an exemplary embodiment. Implant 410 is usable, for example, between and/or within vertebral bodies of the spine, and may share many of the features of the other inter/intra-body implants discussed elsewhere herein. It should be understood that implant 410 may in some embodiments be usable in other portions of the body in addition to the spine, and all such applications are to be understood to be within the scope of the present disclosure. Implant 410 is generally similar to implants 260 and 310 (and the other implants described herein) in structure and function except with respect to the additional longitudinal taper features discussed below. As such, implant 410 is understood to include any or all of the features of the other implants described herein to the extent consistent with the additional features of implant 410 described herein (e.g., retention pins, dovetail projections and ramped surfaces, alignment features, control member access port(s), etc.).

According to an exemplary embodiment, implant 410 includes a first, or front portion 412, a second, or rear portion 414, and a third, intermediate, or control member or portion 416, which collectively form a body or control assembly that extends along a longitudinal axis of implant 410. In some embodiments, front portion 412 includes a through hole 431 configured to enable control member 416 to extend through front portion 412. A first, or upper support 418 (e.g., an upper plate or support member, etc.) and a second, lower support 420 (e.g., a lower plate or support member), are coupled to the body or control assembly and may extend generally between front and rear portions 412, 414. According to an exemplary embodiment, first and second supports 418, 420 define a height of implant 410 extending between the outer or top surface of first support 418 and the outer or lower surface of second support 420. As discuss in greater detail below, the height of implant 410 decreases in a longitudinal direction (e.g., to provide a longitudinal taper feature).

Figure 57:
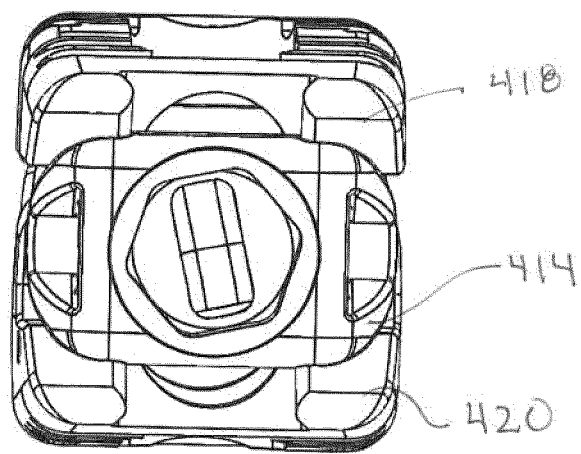
Figure 58:
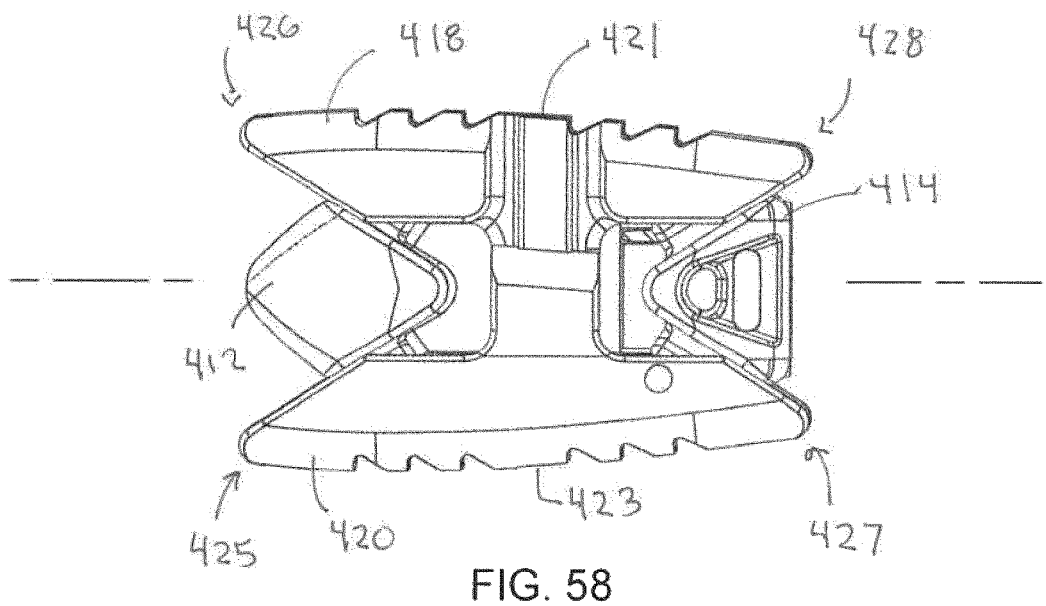
Figure 59:
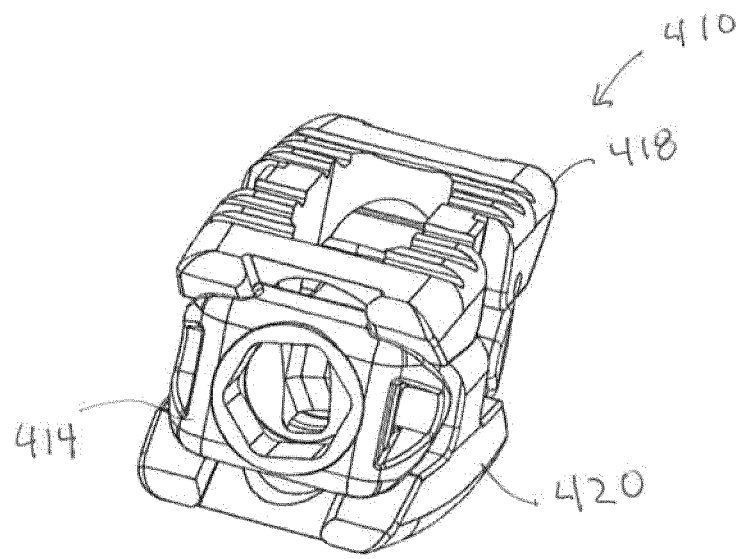
Figure 60:
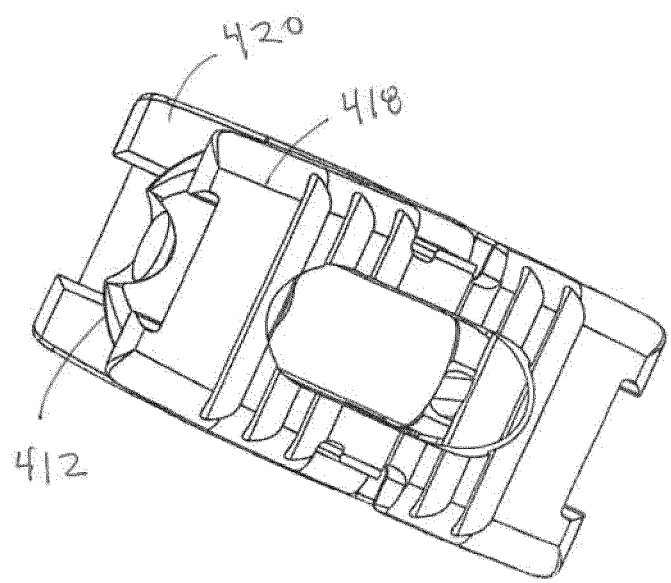

In one embodiment, implant 410 is configured to provide a predetermined longitudinal taper that remains constant as implant 410 is moved between a collapsed configuration (see FIGS. 54-55) and an expanded configuration (see FIGS. 57-58). As such, both the top and bottom supports 418, 420 may include outer surfaces (e.g. top and bottom surfaces) that define a lateral angular offset from a parallel configuration (e.g., a configuration where the top and bottom supports 418, 420 are generally parallel).

In some embodiments, implant 410 defines a longitudinal axis extending along control member 416. Top support 418 defines a first end 426, a second end 428, and a top surface 421 extending between first and second ends 426, 428. First and second ends 426, 428 define an overall taper to top surface 421. In some embodiments, top surface 421 may define an arcuate shape between first end 426 and second end 428 (e.g., such that top surface 421 has a slight curvature between first and second ends 426, 428). In other embodiments, top surface 421 may define a substantially planar surface between first and second ends 426, 428. Bottom support 420 defines a first end 425, a second end 427, and a bottom surface 423 extending between first and second ends 425, 427. First and second ends 425, 427 define an overall taper to top surface 423. In some embodiments, top surface 423 may define an arcuate shape between first end 425 and second end 427 (e.g., such that top surface 423 has a slight curvature between first and second ends 425, 427). In other embodiments, top surface 423 may define a substantially planar surface between first and second ends 425, 427.

As shown in FIGS. 54-58, top and bottom supports 418 and 420 move toward and away from each other in a linear manner, such that the degree of taper remains constant. In other embodiment, other configurations may be utilized to provide non-linear movement and a varying longitudinal taper. Furthermore, while FIGS. 54-58 illustrate an implant having a constant longitudinal taper, according to various alternative embodiments, implants may be provided having a variable longitudinal taper.

Figure 61:
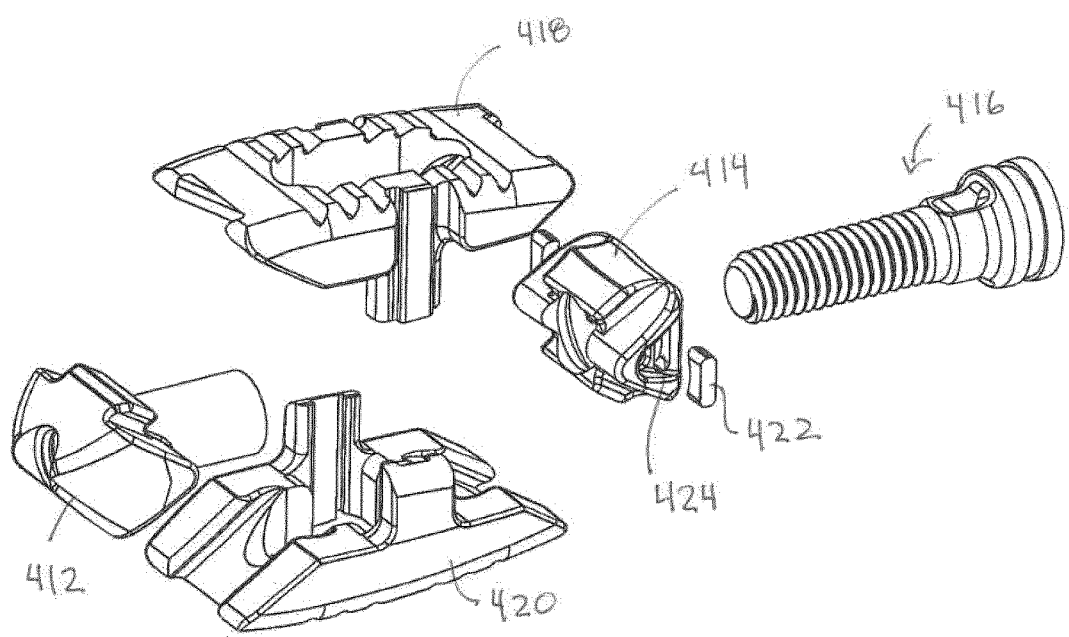
Figure 62:
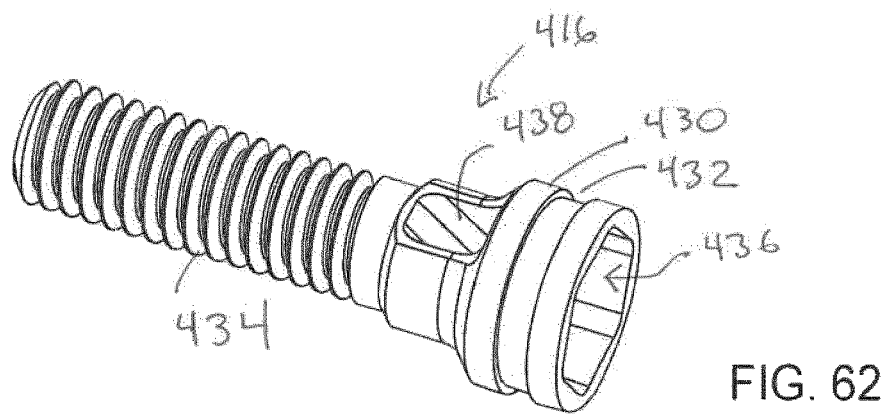
Figure 63:
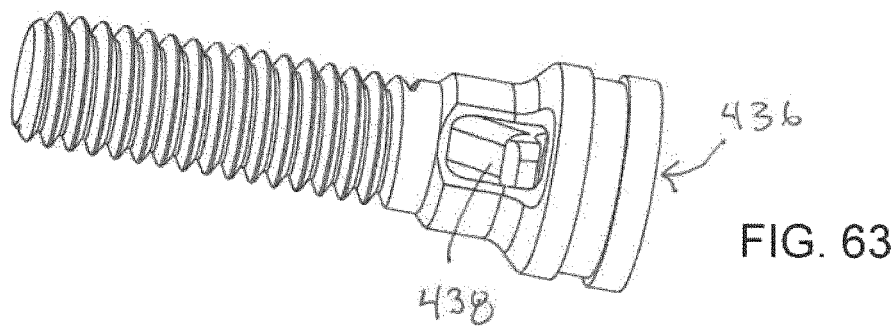
Figure 64:
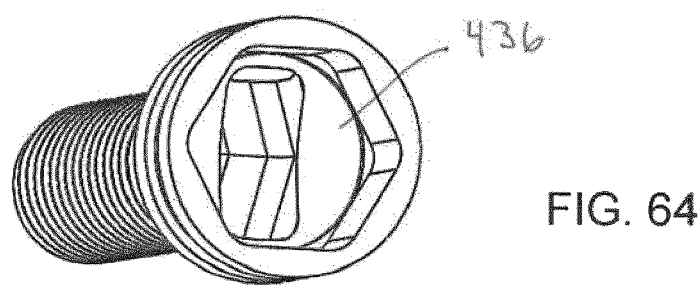
Figure 65:
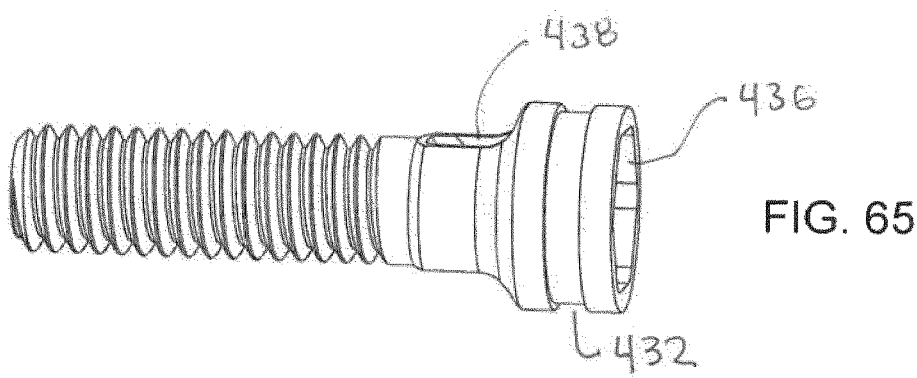
Figure 66:
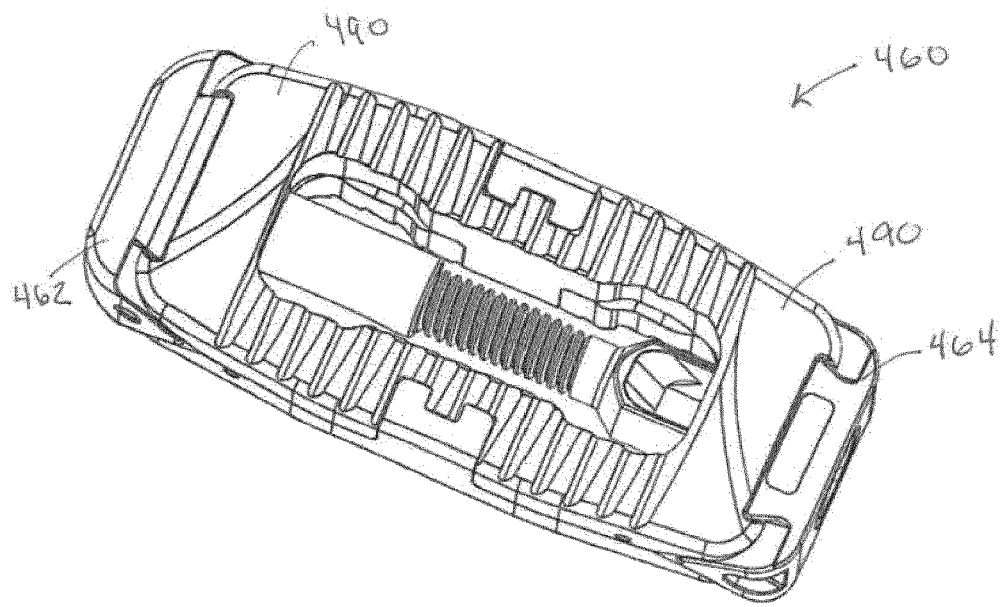
FIGS. 66-70 show various views of an expandable implant according to an alternative embodiment.
Figure 67:
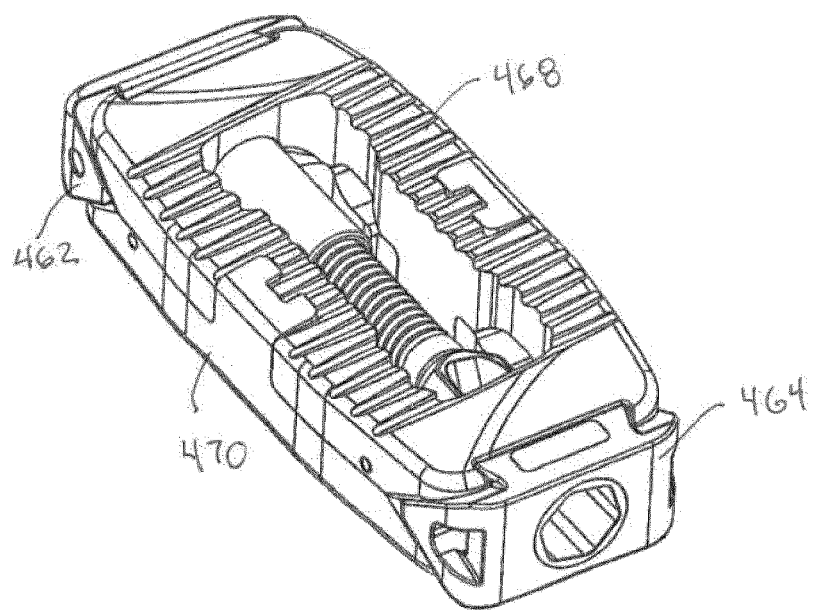
Figure 68:
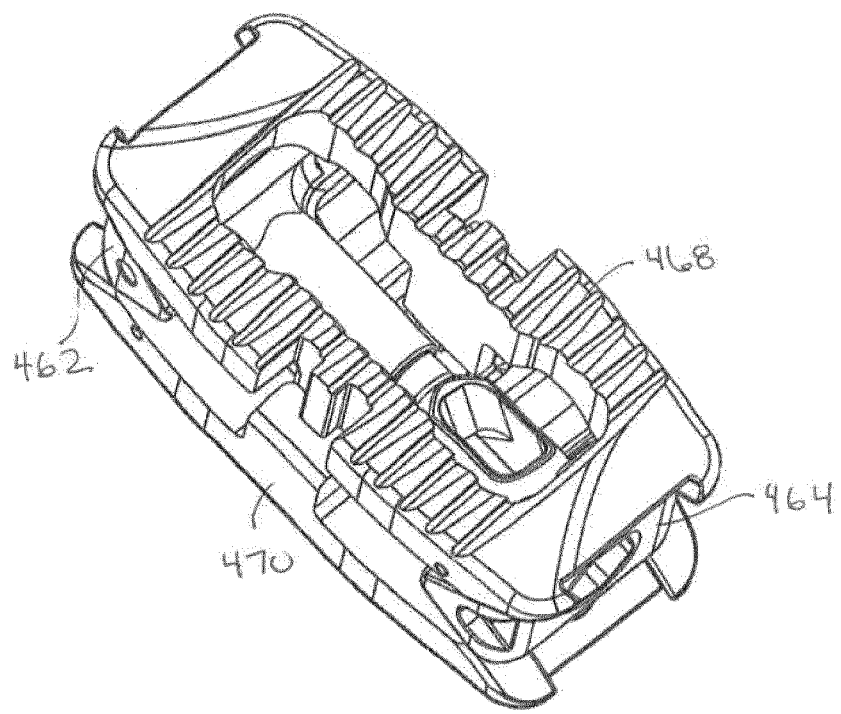

Referring to FIGS. 61-65, in some embodiments, implant 410 includes one or more retaining members to retain control member 416 in a desired longitudinal position. For example, as shown in FIG. 61, in one embodiment, implant 410 includes retaining members 422 received in side apertures 424 on opposing sides of rear support 414. Control member 416 includes a head portion 430, a groove 432, and a threaded portion 434. Control member 416 further includes a tool recess 436 in fluid communication with access ports 438. Retaining members 422 are configured to extend through rear support 414 and be received within groove 432 of control member 416, such that control member 416 is longitudinally fixed relative to rear support 414, but also rotatable relative to rear support 414. FIG. 61 illustrates retaining members 422 extending into rear support 414 from opposing lateral sides. In various alternative embodiments, retaining members may be used that extend through other portions, such as opposing top and bottom sides.

For example, referring to FIGS. 66-70, an implant 460 is shown according to an exemplary embodiment. Implant 460 is usable, for example, between and/or within vertebral bodies of the spine, and may share many of the features of the other inter/intra-body implants discussed elsewhere herein. It should be understood that implant 460 may in some embodiments be usable in other portions of the body in addition to the spine, and all such applications are to be understood to be within the scope of the present disclosure. Implant 460 is generally similar to the other implants described herein in structure and function except with respect to the additional retaining member features discussed below. As such, implant 460 is understood to include any or all of the features of the other implants described herein to the extent consistent with the additional features of implant 460 described herein (e.g., retention pins, dovetail projections and ramped surfaces, alignment features, control member access port(s), etc.).

According to an exemplary embodiment, implant 460 includes a first, or front portion 462, a second, or rear portion 464, and a third, intermediate, or control member or portion 466, which collectively form a body or control assembly that extends along a longitudinal axis of implant 460. A first, or upper support 468 (e.g., an upper plate or support member, etc.) and a second, lower support 470 (e.g., a lower plate or support member), are coupled to the body or control assembly and may extend generally between front and rear portions 462, 464. According to an exemplary embodiment, first and second supports 468, 470 define a height of implant 460 extending between the outer or top surface of first support 468 and the outer or lower surface of second support 470. In some embodiments, top and bottom supports 468, 470 may include tapered corner sections 490, 492 to facilitate insertion/removal of implant 460, etc.

Figure 70:
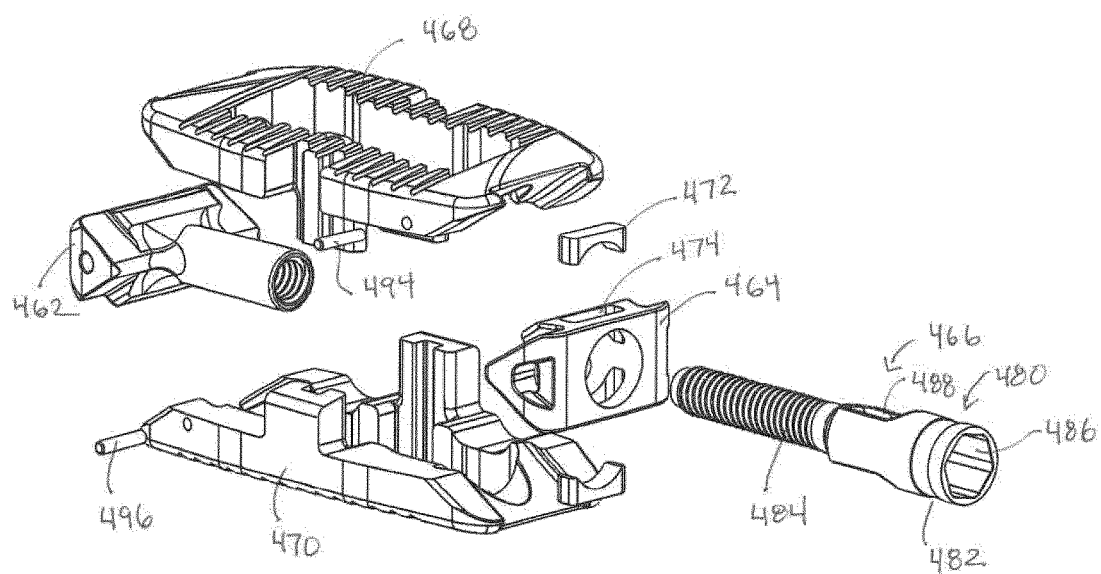

In one embodiment, top and bottom supports 468, 470 are retained by upper and lower pins 494, 496. In one embodiment, upper pins 494 extend through opposite sides of one end of top support 468, and lower pins 496 extend through opposite sides of an opposite end of bottom support 470. Pins 494, 496 act to limit expansion of implant 460 and prevent removal of top and bottom supports 468, 470 from front and rear portions 462, 464. As shown in FIG. 70, in one embodiment, two retaining pins extend into each side of implant 460. In other embodiments, other numbers of retaining pins may be used, as shown for example in various other embodiments herein.

Referring further to FIG. 70, in some embodiments, implant 460 includes one or more retaining members to retain control member 466 in a desired longitudinal position. For example, as shown in FIG. 70, in one embodiment, implant 460 includes retaining members 472 received in top and bottom apertures 474 on opposing top and bottom sides of rear support 464. Control member 466 includes a head portion 480, a groove 482, and a threaded portion 484. Control member 466 further includes a tool recess 486 in fluid communication with access ports 488. Retaining members 472 are configured to extend through rear support 464 and be received within groove 482 of control member 466, such that control member 466 is longitudinally fixed relative to rear support 464, but also rotatable relative to rear support 464. FIG. 70 illustrates retaining members 472 extending into rear support 464 from opposing top and bottom sides. In various alternative embodiments, retaining members may be used that extend through other portions, such as opposing lateral sides. (e.g., as discussed with respect to implant 410)

Referring now to FIGS. 71-75, an implant 510 is shown according to an exemplary embodiment. Implant 510 is usable, for example, between and/or within vertebral bodies of the spine, and may share many of the features of the other inter/intra-body implants discussed elsewhere herein. It should be understood that implant 510 may in some embodiments be usable in other portions of the body in addition to the spine, and all such applications are to be understood to be within the scope of the present disclosure. Implant 510 is generally similar to the other implants discussed herein in structure and function except with respect to the two-piece top and bottom support member features discussed below. As such, implant 510 is understood to include any or all of the features of the other implants described herein to the extent consistent with the additional features of implant 510 described herein.

According to an exemplary embodiment, implant 510 includes a first, or front portion 512, a second, or rear portion 514, and a third, intermediate, or control member or portion 516, which collectively form a body or control assembly that extends along a longitudinal axis of implant 510. A first, or upper support assembly 518 (e.g., an upper plate or support member, etc.) and a second, lower support assembly 520 (e.g., a lower plate or support member), are coupled to the control assembly and may extend generally between front and rear portions 512, 514. According to an exemplary embodiment, first and second support assemblies 518, 520 define a height of implant 520 extending between the outer or top surface of first support assembly 518 and the outer or lower surface of second support assembly 520.

Front portion 512 includes ramped surfaces 562 and a threaded bore 564. Rear portion 514 includes dovetailed projections 566 and recess or aperture 568. Ramped surfaces 562 and dovetailed projections 566 facilitate controlled expansion and contraction of top support assembly 518 and bottom support assembly 520 relative to one another.

In one embodiment, top support assembly 518 includes a first portion 522 and a second portion 524 pivotally coupled to first portion 522 by way of a top pivot pin 530. First portion 522 defines an extension portion 532 that at least partially extends into a recess 534 in second portion 524. Top guide pins 526 extend through second portion 524 and into upper slots 528 in first portion 522 to limit the range of pivotal motion of first portion 522 relative to second portion 524 about top pivot pin 530. First portion 522 includes a ramped surface 536, and second portion 524 includes a dovetailed recess 538. Ramped surface 536 slidingly interfaces with a corresponding ramped surface 562 on front portion 512, and dovetailed recess 538 slidingly interfaces with a dovetailed projection 566 on rear portion 514.

In one embodiment, bottom support assembly 520 includes a first portion 542 and a second portion 544 pivotally coupled to first portion 542 by way of a bottom pivot pin 550. First portion 542 defines an extension portion 552 that at least partially extends into a recess 554 in second portion 524. Bottom guide pins 546 extend through second portion 544 and into bottom slots 548 in first portion 542 to limit the range of pivotal motion of first portion 542 relative to second portion 544 about bottom pivot pin 550. First portion 542 includes a ramped surface 556, and second portion 524 includes a dovetailed recess 558. Ramped surface 556 slidingly interfaces with a corresponding ramped surface 562 on front portion 512, and dovetailed recess 558 slidingly interfaces with a dovetailed projection 566 on rear portion 514.

In one embodiment, implant 510 includes alignment features configured to maintain proper alignment between at least a portion of top support assembly 518 and at least a portion of bottom support assembly 520. For example, an upper alignment guide 540 on second portion 524 of top support assembly 518 slidingly engages a correspondingly shaped lower alignment guide 560 on second portion 544 of bottom support assembly 520. As such, as first portions 522 and 542 angulate away from each other, second portions 524, 544 remain aligned (e.g., move in a linear fashion relative to one another).

Figure 71:
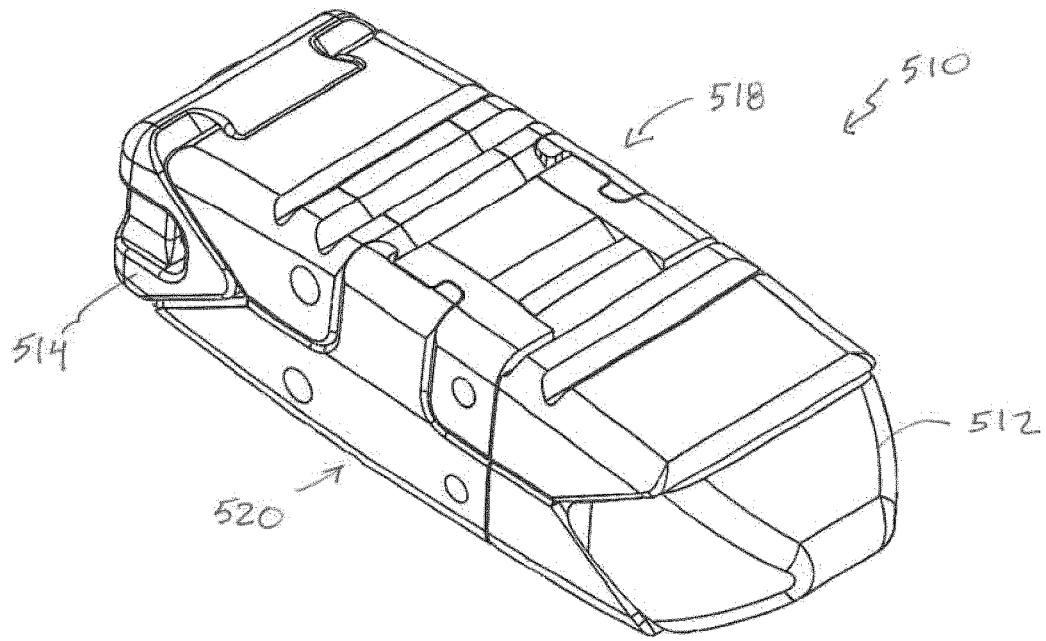
FIGS. 71-75 show various views of an expandable implant according to an alternative embodiment.
Figure 72:
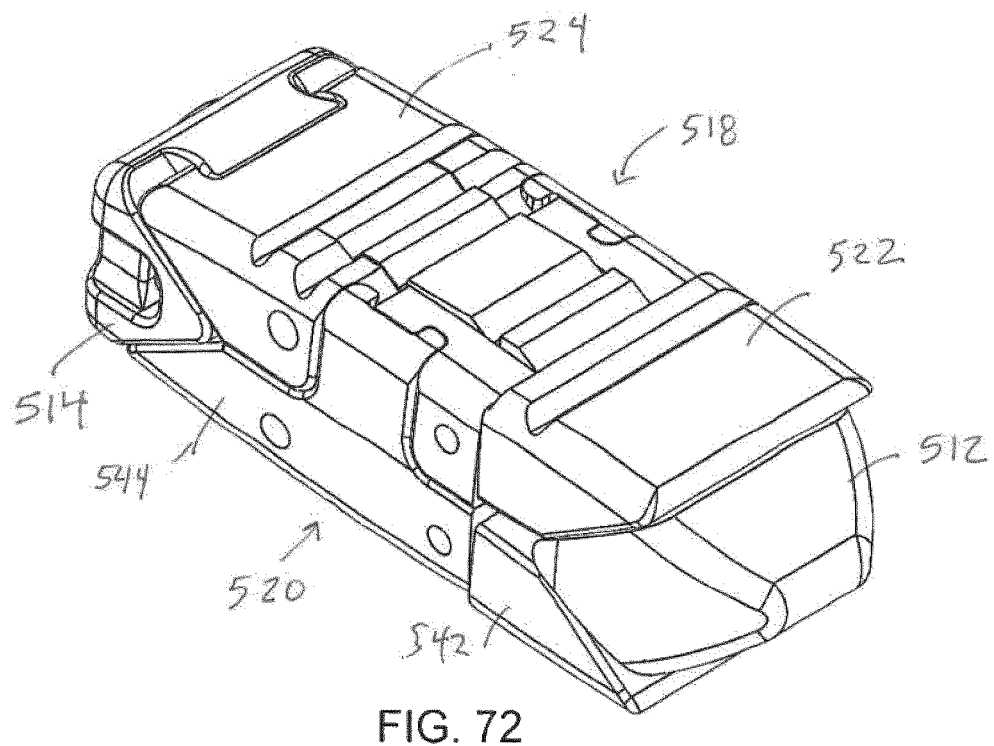
Figure 73:
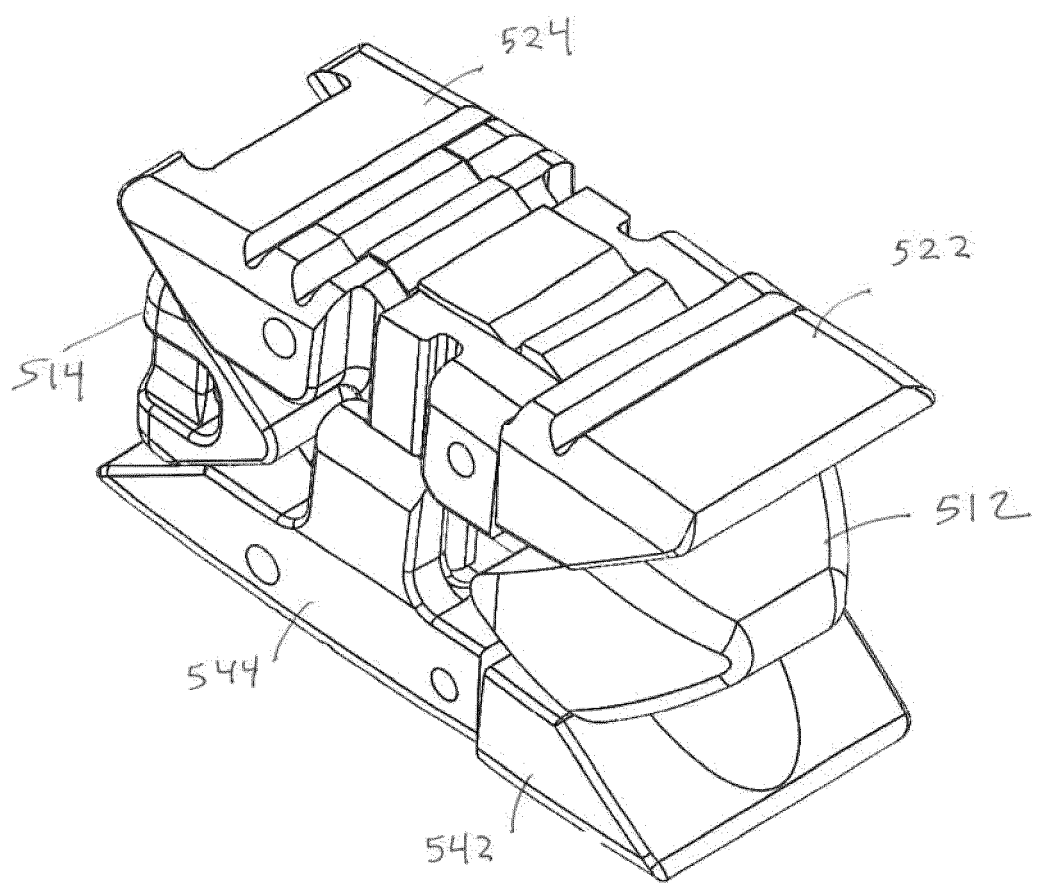
Figure 74:
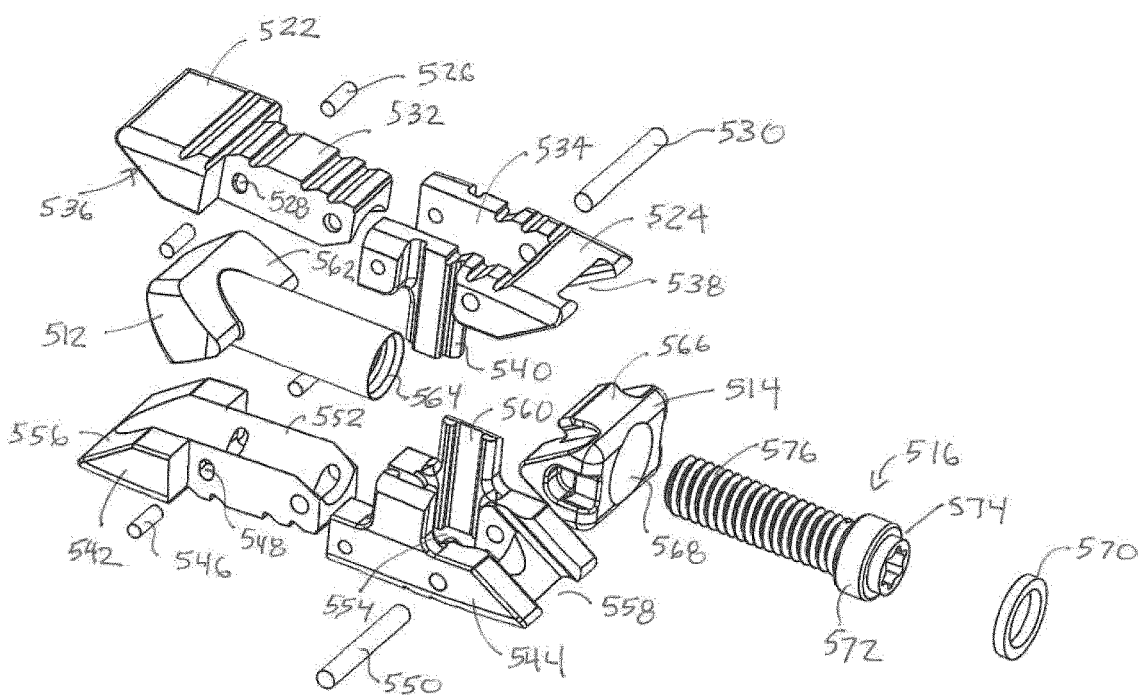
Figure 75:
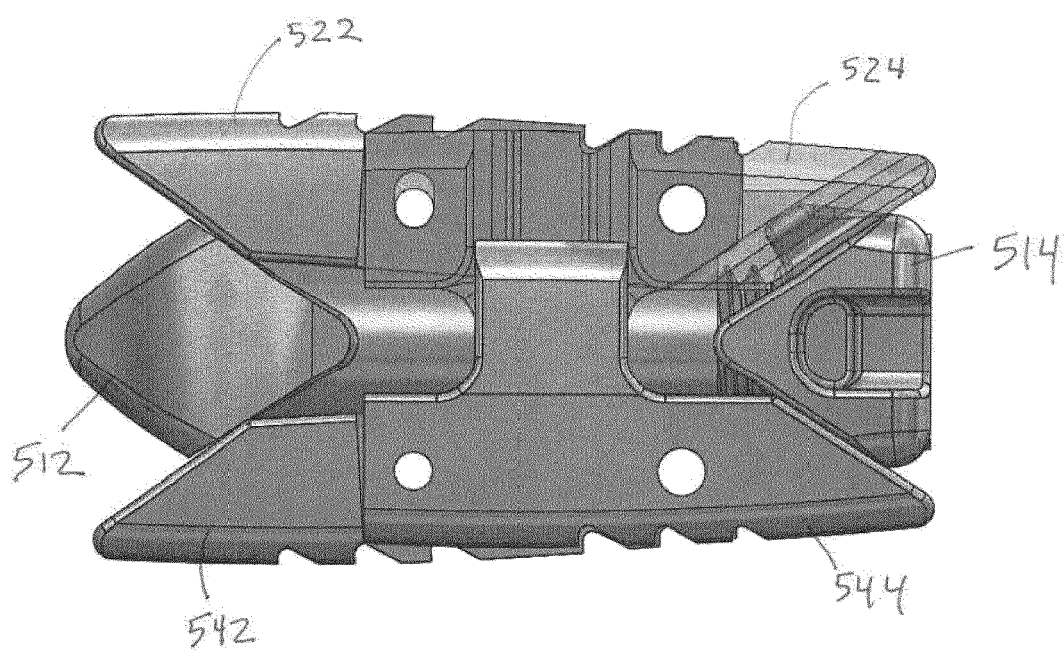

In one embodiment, implant 510 is moveable from a first, fully collapsed and aligned position, as shown in FIG. 71, to a second, collapsed and angulated position, as shown in FIG. 72, to a third, expanded and angulated position, as shown in FIG. 73. Implant 510 may be positioned at any desired intermediate position between the first, second, and third positions. In use, a first amount of rotation of control member 516 causes angulation of first portions 522, 542 relative to second portions 524, 544. As control member 516 is threaded into threaded bore 564, first portion 522 rotates about top pivot pin 530 and first portion 542 rotates about bottom pivot pin 550. First portions 522, 542 continue to angulate until top and bottom guide pins 526, 546 are retained by upper and lower slots 528, 548, which define the maximum amount of angulation for first portions 522, 542.

Once maximum angulation is reached, further rotation of control member 516 causes expansion of second members 524, 544 (and therefore also first members 522, 542) relative to one another in a generally linear fashion (e.g., through the interaction of alignment guides 540, 560). It should be noted that to enable angulation of first portions 522, 542, front portion 512 and first portions 522, 542 have generally flat, correspondingly shaped ramped surfaces 562 (on front portion 512), 536 (on first portion 522 of top support assembly 518), and 556 (on first portion 542 of bottom support assembly 520). To facilitate linear movement of second portions 524, 544, rear portion 514 includes dovetailed projections 566, which are received within dovetailed recesses 438 (on second portion 524 of top support assembly 518) and 558 (on second portion 544 of bottom support assembly 520).

The angulation and expansion features enable a user to initially install implant 510 in a collapsed, aligned position, as shown in FIG. 71, which may facilitate initial insertion and adjustment of the device. Once in proper position, implant 510 may be moved to a desired angulated and/or expanded configuration, as shown in FIGS. 72 and 73. In the fully expanded and angulated position, as shown in FIG. 73, the outer surfaces (e.g., top and bottom surfaces) of first portions 522, 542 are offset (e.g. angularly offset) from the outer surfaces of second portions 524, 544, and angularly offset from the longitudinal axis of implant 510 (e.g., an axis extending along control member 516). The amount of angulation may be varied to suit a particular application (e.g., an amount of spinal curvature to be accommodated by the implant, etc.).

Referring now to FIGS. 76-83, an implant 610 is shown according to an exemplary embodiment. Implant 610 is usable, for example, between and/or within vertebral bodies of the spine, and may share many of the features of the other inter/intra-body implants discussed elsewhere herein. It should be understood that implant 610 may in some embodiments be usable in other portions of the body in addition to the spine, and all such applications are to be understood to be within the scope of the present disclosure. Implant 610 is generally similar to the other implants discussed herein in structure and function except with respect to the two-piece top and bottom support member and specific control member features discussed below. As such, implant 610 is understood to include any or all of the features of the other implants described herein to the extent consistent with the additional features of implant 610 described herein.

According to an exemplary embodiment, implant 610 includes a first, or front portion 612, a second, or rear portion 614, a first, or inner, control member 615, a second, or outer, control member 616, and a receiver member 617, which collectively form a body or control assembly that extends along a longitudinal axis of implant 610. A first, or upper support assembly 618 (e.g., an upper plate or support member, etc.) and a second, lower support assembly 620 (e.g., a lower plate or support member), are coupled to the control assembly and may extend generally between front and rear portions 612, 614. According to an exemplary embodiment, first and second support assemblies 618, 620 define a height of implant 610 extending between the outer or top surface of first support assembly 618 and the outer or lower surface of second support assembly 620.

Front portion 612 includes ramped surfaces 654 and a receiver recess or bore 656. Rear portion 614 includes ramped surfaces 658 and control recess or bore 660. Ramped surfaces 654, 658 facilitate controlled expansion and contraction of top support assembly 618 and bottom support assembly 620 relative to one another.

In one embodiment, top support assembly 618 includes a first or inner portion 622 and a second or outer portion 624 pivotally coupled to first portion 622 by way of a top pivot pin 626. First portion 622 at least partially extends into a recess 628 in second portion 624. First portion 622 includes a ramped surface 630, and second portion 624 includes a ramped surface 632. Ramped surface 630 slidingly interfaces with a corresponding ramped surface 654 on front portion 612, and ramped surface 632 slidingly interfaces with a corresponding ramped surface 658 on rear portion 614.

In one embodiment, bottom support assembly 620 includes a first or inner portion 638 and a second or outer portion 640 pivotally coupled to first portion 638 by way of a bottom pivot pin 642. First portion 638 at least partially extends into a recess 644 in second portion 640. First portion 638 includes a ramped surface 646, and second portion 640 includes a ramped surface 648. Ramped surface 646 slidingly interfaces with a corresponding ramped surface 654 on front portion 612, and ramped surface 648 slidingly interfaces with ramped surface 658 on rear portion 614.

In one embodiment, implant 610 includes alignment features configured to limit a degree of angulation of second portions 624, 640 relative to first portions 622, 638. For example, in some embodiments, first portion 622 of top support assembly 618 includes a single alignment guide or member 634 that is received between two alignment guides or members 650 on first portion 638 of bottom support assembly 620. Alignment guides 634, 650 are collectively received in a top alignment recess in second portion 624 of top support assembly 618 and a bottom alignment recess 644 in second portion 640 of bottom support assembly 620. The various alignment components may be configured to enable a predetermined amount of angulation between first portions 622, 63 and second portions 624, 640.

Figure 76:
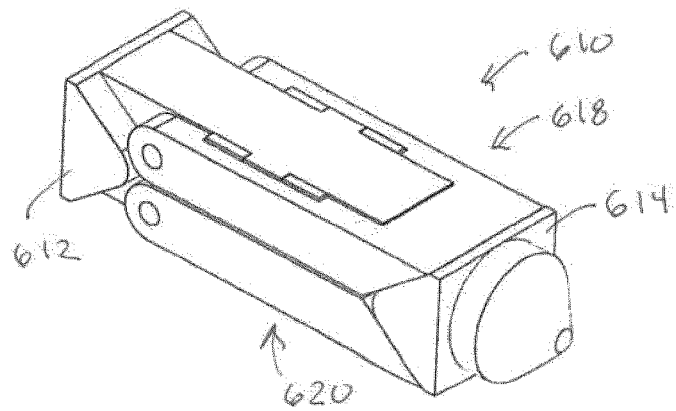
FIGS. 76-83 show various views of an expandable implant according to an alternative embodiment.
Figure 77:
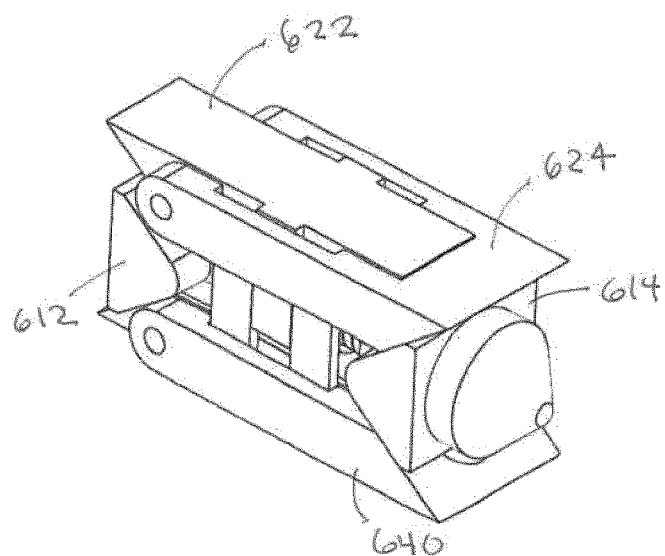
Figure 78:
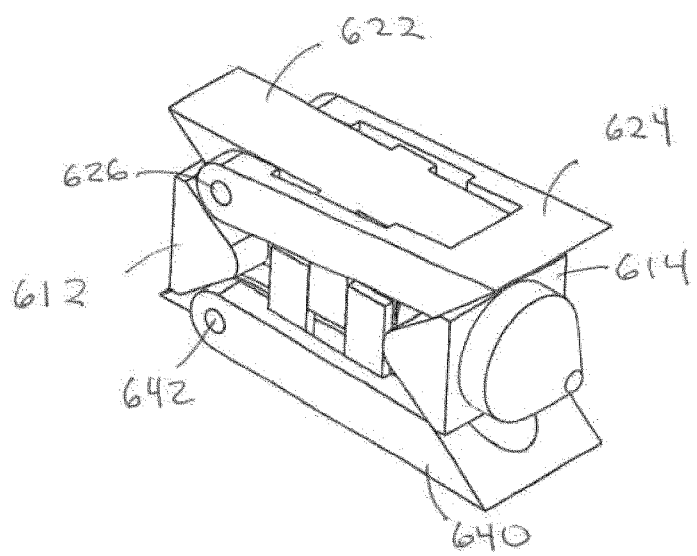
Figure 79:
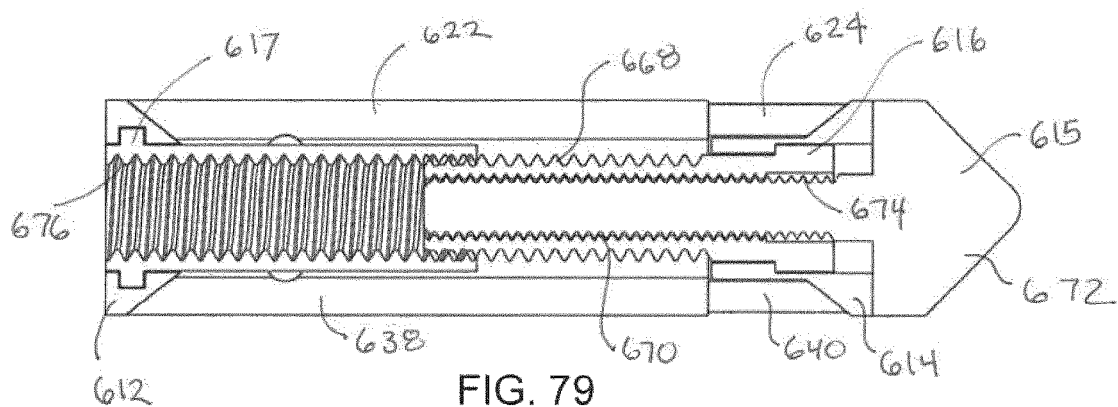
Figure 80:
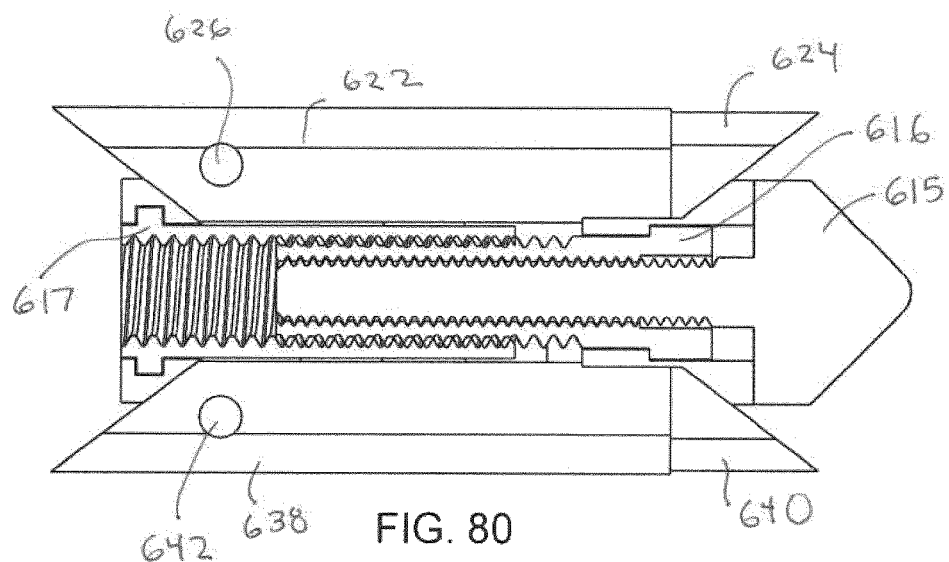
Figure 81:
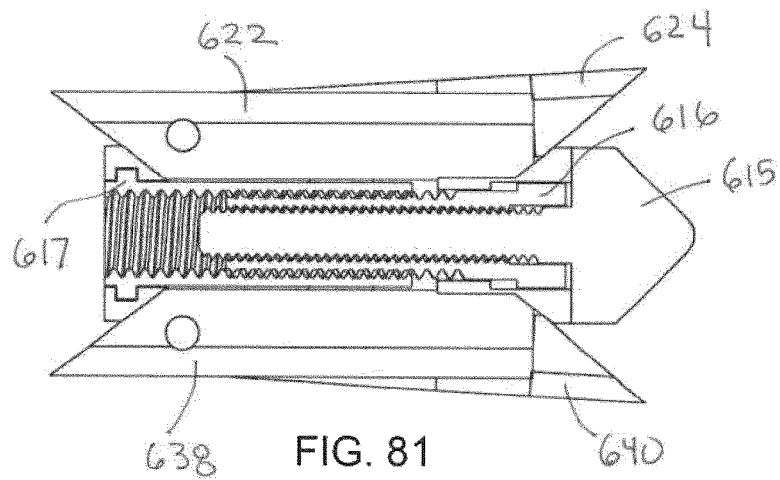
Figure 82:
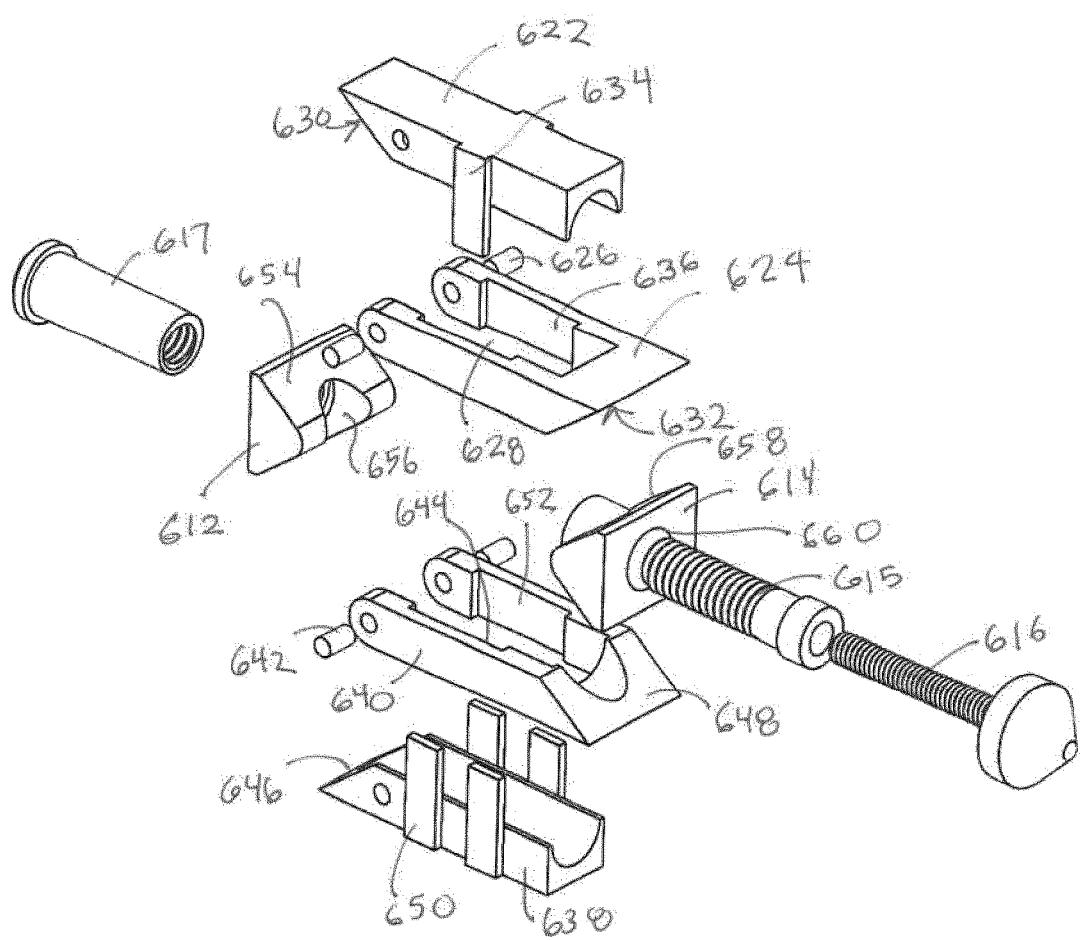
Figure 83:
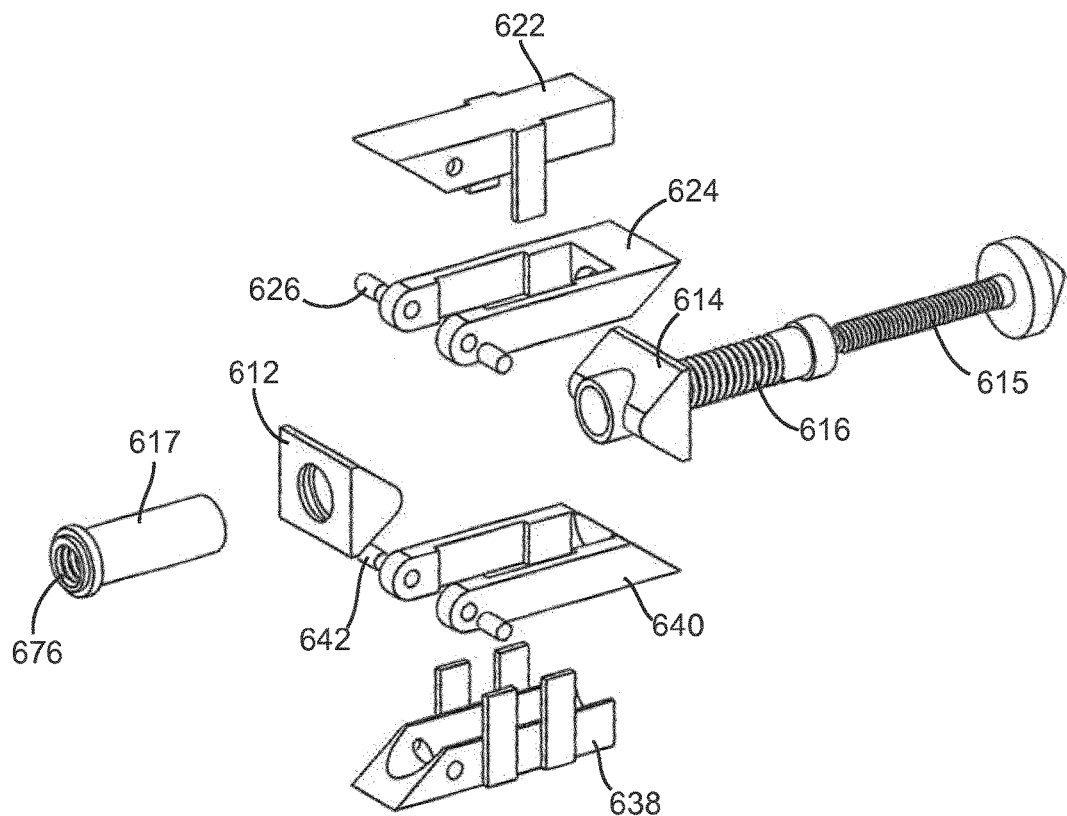

In one embodiment, implant 610 is moveable from a first, fully collapsed and aligned position, as shown in FIGS. 76 and 79, to a second, expanded and aligned position, as shown in FIGS. 77 and 80, to a third, expanded and angulated position, as shown in FIGS. 78 and 81. Implant 610 may be positioned at any desired intermediate position between the first, second, and third positions. Furthermore, the order of expansion and angulation may be reversed, or alternated, during installation.

In use, threading of outer control member 616 into (or out of) receiver 617 causes linear relative movement (e.g., expansion or contraction) of top support assembly 618 and bottom support assembly 620. For example, FIGS. 77 and 80 show implant 610 with outer control member 616 having been threaded into receiver 617 by way of threading engagement of the outer threads 668 of outer control member 616 and the inner threads 676 of receiver 617. As front portion 612 and rear portion 614 move toward/away from each other, top and bottom support assemblies 618, 620 likewise move away from/toward each other.

Threading of inner control member 615 within outer control 616 member causes second portions 624, 640 to angulate relative to first portions 622, 638. For example, FIGS. 78 and 81 show implant 610 with inner control member 615 having been threaded into outer control member 616, causing second portions 624, 640 to rotate about top and bottom pivot pins 626, 642, causing second portions 624, 640 to become angularly offset relative to first portions 622, 638.

Figure 69:
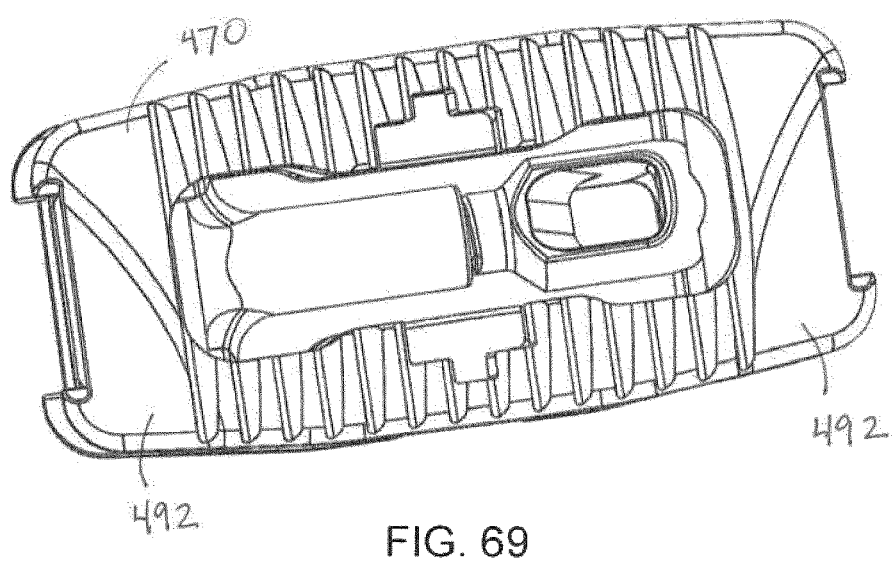

The angulation and expansion features enable a user to initially install implant 610 in a collapsed, aligned position, as shown in FIGS. 76 and 69, which may facilitate initial insertion and adjustment of the device. Once in proper position, implant 610 may be moved to a desired angulated and/or expanded configuration, as shown in FIGS. 77-78 and 80-81. In the fully expanded and angulated position, as shown in FIGS. 78 and 81, the outer surfaces (e.g., top and bottom surfaces) of second portions 624, 640 are offset (e.g. angularly offset) from the outer surfaces of first portions 622, 638, and angularly offset from the longitudinal axis of implant 610 (e.g., an axis extending along outer control member 616). The amount of angulation may be varied to suit a particular application (e.g., an amount of spinal curvature to be accommodated by the implant, etc.).

Figure 84:
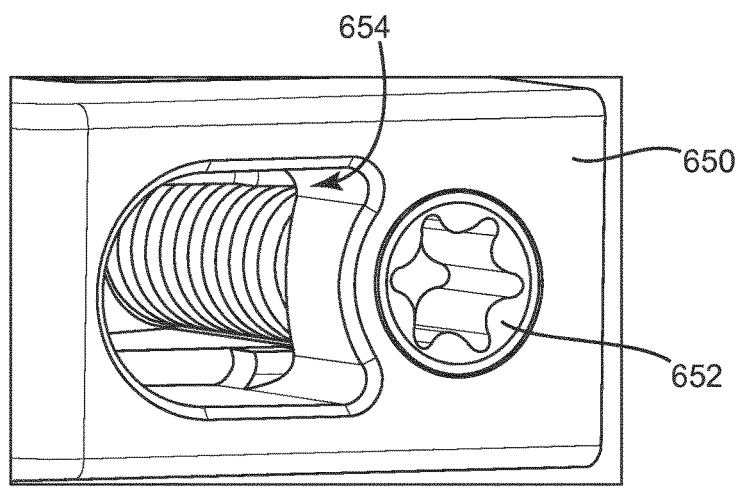
FIG. 84 shows a portion of an expandable implant according to an alternative embodiment.

Referring now to FIG. 84, a portion of an implant is shown according to an exemplary embodiment. In one embodiment, the portion includes a member 650, which may be similar to various components described with respect to the various other embodiments disclosed herein. For example, member 650 may form part of a control assembly and act as a rear member similar to rear portions 14, 114, 214, etc. As shown in FIG. 84, access to the interior of the various implants disclosed herein may be by way of member 650. Member 650 includes a control member 652 and an access aperture 654. Control member 652 acts to control expansion and contraction of the implant, and aperture 654 enables access to the interior of the implant. The access features of member 650 may be implemented in any of the implant components described herein, including the various front and rear portions, top and bottom supports, etc. All such combinations of features are to be understood to be within the scope of the present disclosure.

It is important to note that the construction and arrangement of the elements of the various implants and implant components as shown in the exemplary embodiments are illustrative only. Although a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the various embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. An expandable implant, comprising:
   a top support configured to engage a first portion of vertebral bone;
   a bottom support configured to engage a second portion of vertebral bone;
   a control assembly coupled to the top support and the bottom support and configured to control relative movement between the top support and the bottom support, wherein the control assembly includes a control member including a head and a body portion;
   wherein the head includes a recess and the body portion includes at least one access port in fluid communication with the recess to enable delivery of fluid to an interior of the implant via the recess and at least one access port;
   wherein the control assembly further comprises a front portion adjustably coupled to the body portion of the control member and a rear portion longitudinally fixed relative to the head of the control member.

2. The implant of claim 1, wherein the access port includes a pair of access ports provided on generally opposite sides of the body portion.

3. The implant of claim 2, wherein the recess extends along a longitudinal axis defined by the control member, and wherein each access port extends from the recess in a non-perpendicular fashion relative to the longitudinal axis.

4. The implant of claim 1, further comprising a retaining member extending through the rear portion and engaging a circumferential groove in the head of the control member.

5. The implant of claim 4, wherein the retaining member includes a pair of retaining members.

6. The implant of claim 4, wherein the retaining member extends through at least one of a top and bottom portion of the rear portion.

7. The implant of claim 4, wherein the retaining member extends through at least one lateral side portion of the rear portion.

8. The implant of claim 1, wherein the implant is generally symmetric about at least one plane extending along the control assembly.

9. The implant of claim 1, wherein the implant is asymmetric about at least one plane extending along the control assembly.

10. An expandable implant, comprising:
    a top support including a top surface configured to engage a first portion of vertebral bone;
    a bottom support including a bottom surface configured to engage a second portion of vertebral bone, wherein the top and bottom surfaces define a taper; and
    a control assembly coupled to the top support and the bottom support and configured to control relative movement between the top support and the bottom support, wherein the control assembly includes a control member having a recess and at least one access port in fluid communication with the recess to enable delivery of fluid to an interior of the implant via the recess and at least one access port;
    wherein the control assembly comprises a front portion threadingly coupled to a threaded portion of the control member and a rear portion rotatably coupled and longitudinally fixed relative to a head of the control member.

11. The implant of claim 10, wherein the taper remains constant during movement of the top support relative to the bottom support.

12. The implant of claim 11, wherein the taper extends in a direction generally parallel to a longitudinal axis of the control assembly.

13. The implant of claim 11, wherein the taper extends in a direction generally perpendicular to a longitudinal axis of the control assembly.

14. The implant of claim 10, further comprising a retaining member extending through the rear portion and engaging a circumferential groove in the head of the control member.

15. An implant comprising,
    a top support configured to engage a first portion of vertebral bone;
    a bottom support configured to engage a second portion of vertebral bone;

a control assembly coupled to the top support and the bottom support and configured to control relative movement between the top support and the bottom support, wherein the control assembly includes:
- a front portion configured to slidably engage the top and bottom supports;
- a rear portion configured to slidably engage the top and bottom supports; and
- a control member including a head disposed within the rear portion, and a threaded portion threadingly engaging the front portion;

wherein the head includes a recess and at least one access port in fluid communication with the recess to enable delivery of fluid to an interior of the implant via the recess and at least one access port.

16. The implant of claim 15, wherein the top and bottom supports define a general taper of the implant extending between the front portion and the rear portion.

17. The implant of claim 15, wherein the top and bottom supports define a general taper extending between lateral sides of the top and bottom supports.

18. The implant of claim 15, further comprising at least one retaining member configured to extend through the rear portion and engage a circumferential groove in the head of the control portion.

* * * * *